(12) United States Patent
Tian et al.

(10) Patent No.: US 8,318,306 B2
(45) Date of Patent: *Nov. 27, 2012

(54) SUPERABSORBENT POLYMER COMPOSITIONS HAVING A TRIGGERING COMPOSITION

(75) Inventors: Gonglu Tian, Greensboro, NC (US);
Scott J. Smith, Greensboro, NC (US);
Yaru Shi, Greensboro, NC (US);
Richard N. Dodge, Appleton, WI (US);
Jian Qin, Appleton, WI (US)

(73) Assignee: Evonik Stockhausen, LLC, Greensboro, NC (US)

( * ) Notice: Subject to any disclaimer, the term of this patent is extended or adjusted under 35 U.S.C. 154(b) by 989 days.

This patent is subject to a terminal disclaimer.

(21) Appl. No.: 12/022,699

(22) Filed: Jan. 30, 2008

(65) Prior Publication Data
US 2009/0191408 A1 Jul. 30, 2009

(51) Int. Cl.
*B32B 19/00* (2006.01)
*B32B 23/02* (2006.01)
*B32B 27/02* (2006.01)
*A61F 13/15* (2006.01)
*A61F 13/20* (2006.01)

(52) U.S. Cl. ........ 428/407; 428/402; 428/403; 604/364; 604/367; 604/369; 604/372; 604/376

(58) Field of Classification Search ............... 604/376
See application file for complete search history.

(56) References Cited

U.S. PATENT DOCUMENTS

| | | | |
|---|---|---|---|
| 5,451,613 A | 9/1995 | Smith et al. | |
| 5,462,972 A | 10/1995 | Smith et al. | |
| 6,646,179 B1 * | 11/2003 | Melius et al. | 604/368 |
| 6,696,618 B2 | 2/2004 | Dodge, II et al. | |
| 6,906,131 B2 | 6/2005 | Ahmed et al. | |
| 7,163,969 B2 | 1/2007 | Ahmed et al. | |
| 7,169,843 B2 | 1/2007 | Smith et al. | |
| 7,173,086 B2 | 2/2007 | Smith et al. | |
| 7,241,820 B2 | 7/2007 | Smith et al. | |
| 7,291,674 B2 | 11/2007 | Kang et al. | |
| 7,312,286 B2 | 12/2007 | Lang et al. | |
| 7,335,713 B2 | 2/2008 | Lang et al. | |
| 7,399,813 B2 | 7/2008 | Lang et al. | |
| 7,427,650 B2 | 9/2008 | Smith et al. | |

(Continued)

FOREIGN PATENT DOCUMENTS

CA 2460152 A1 3/2003

(Continued)

OTHER PUBLICATIONS

Lide, David R. (editor). CRC Handbook of Chemistry and Physics 91st Edition Internet Version 2011. Copyright 2011, Taylor and Francis Group, LLC. pp. 3-84, 3-85, 4-34, 4-90, 8-35, 8-127.*

(Continued)

*Primary Examiner* — Humera Sheikh
*Assistant Examiner* — Thomas Mangohig
(74) *Attorney, Agent, or Firm* — Smith Moore Leatherwood LLP; Philip P. McCann

(57) ABSTRACT

The present invention relates to absorbent compositions which exhibit swelling, deswelling, and reswelling behavior. More specifically, absorbent compositions of this invention swell and absorb fluids after exposure to aqueous fluids, deswell and release fluids from the swollen absorbent compositions, and may also reswell and absorb fluids. The swelling-deswelling-reswelling behavior allows enhanced liquid distribution in absorbent composites.

23 Claims, 13 Drawing Sheets

Swell/deswell/reswell curves for superabsorbent composition SAP-B and with triggering compositions 1st TC-A and 2nd TC-B

U.S. PATENT DOCUMENTS

| | | | |
|---|---|---|---|
| 7,482,058 B2 | 1/2009 | Ahmed et al. | |
| 7,488,541 B2 | 2/2009 | Ahmed et al. | |
| 7,579,402 B2 | 8/2009 | Ahmed et al. | |
| 2003/0109840 A1* | 6/2003 | Dodge et al. | 604/364 |
| 2003/0139714 A1* | 7/2003 | Sun et al. | 604/368 |
| 2005/0027268 A1 | 2/2005 | Qin et al. | |
| 2005/0137546 A1* | 6/2005 | Joy et al. | 604/368 |
| 2005/0234413 A1* | 10/2005 | Funk et al. | 604/358 |
| 2005/0288182 A1* | 12/2005 | Torii et al. | 502/402 |
| 2006/0173097 A1* | 8/2006 | Ahmed et al. | 523/200 |
| 2007/0066718 A1 | 3/2007 | Smith et al. | |
| 2007/0066754 A1 | 3/2007 | Loeker et al. | |
| 2007/0135554 A1 | 6/2007 | Mcintosh et al. | |
| 2007/0145326 A1* | 6/2007 | Joseph et al. | 252/70 |
| 2007/0167560 A1 | 7/2007 | Smith et al. | |
| 2008/0009616 A1 | 1/2008 | Frank et al. | |
| 2008/0234420 A1 | 9/2008 | Smith et al. | |
| 2009/0023848 A1 | 1/2009 | Ahmed et al. | |
| 2009/0134357 A1 | 5/2009 | Bub et al. | |
| 2009/0191408 A1 | 7/2009 | Tian et al. | |
| 2009/0192481 A1 | 7/2009 | Dodge et al. | |
| 2009/0192482 A1 | 7/2009 | Dodge et al. | |
| 2010/0075844 A1 | 3/2010 | Loeker et al. | |
| 2010/0100066 A1 | 4/2010 | Azad et al. | |
| 2010/0130355 A1 | 5/2010 | Tian et al. | |

FOREIGN PATENT DOCUMENTS

| | | |
|---|---|---|
| CN | ZL02819951 | 8/2007 |
| EP | 1438354 A1 | 7/2004 |
| JP | 62162086 A * | 7/1987 |
| WO | 03025054 A1 | 3/2003 |

OTHER PUBLICATIONS

Lide, David R. (editor). CRC Handbook of Chemistry and Physics 91st Edition Internet Version 2011. Copyright 2011, Taylor and Francis Group, LLC. p. 4-54.*
International Search Report mailed on Apr. 16, 2010 in PCT/US2009/032424.
Tian et al., U.S. Appl. No. 12/256,038, filed Oct. 22, 2008.
Tian et al., U.S. Appl. No. 12/775,984, filed May 7, 2010.
Written Opinion mailed on Apr. 16, 2010 in PCT/US2009/032424.
Ying Zhao et al., "Superabsorbent hydrogels from poly(aspartic acid) with salt-, temperature-, and pH-responsiveness properties," copyright 2005, Polymer, vol. 46, pp. 5368-5376.
Richard N. Dodge III et al., U.S. Appl. No. 12/215,942, filed Jun. 30, 2008, Mar. 7, 2011 Notice of Allowance, Feb. 16, 2011 Response to Office Action, and Sep. 16, 2010 Office Action.
Richard N. Dodge III et al., U.S. Appl. No. 12/217,020, filed Jun. 30, 2008, Mar. 3, 2011 Notice of Allowance, Feb. 15, 2011 Response to Office Action, and Sep. 15, 2010 Office Action.
"Selected Solubility Products and Formation Constants at 25° C.," web page, copyright 2011, pp. 1-7, California State University, Dominguez Hills, Carson, CA, US.

* cited by examiner

FIG 1. Release profiles of poly(meth)acrylate coated sulfamic acid
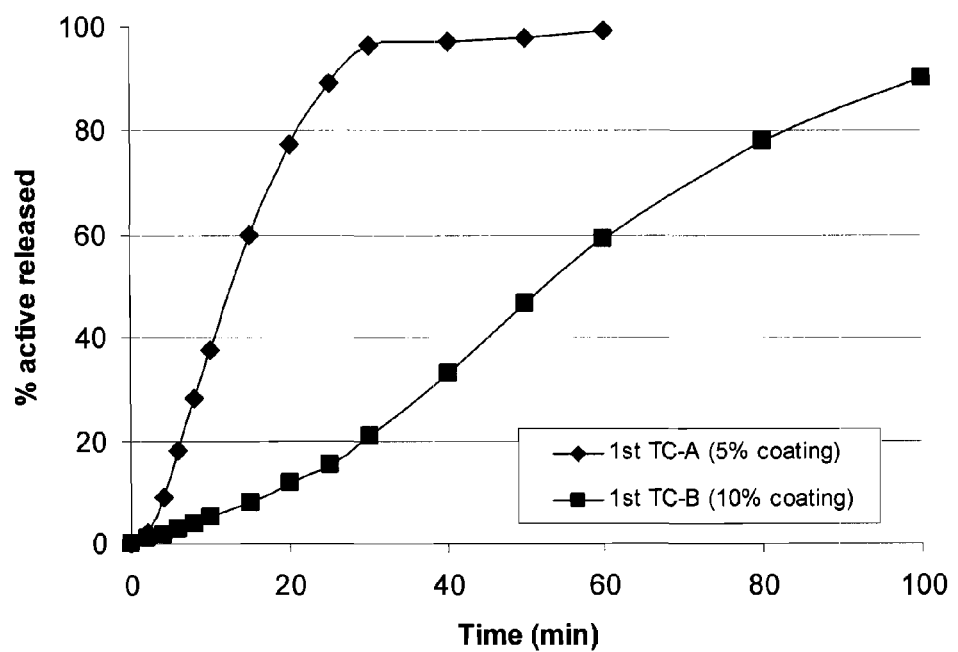

FIG 2. Release profiles of poly(meth)acrylate coated calcium formate
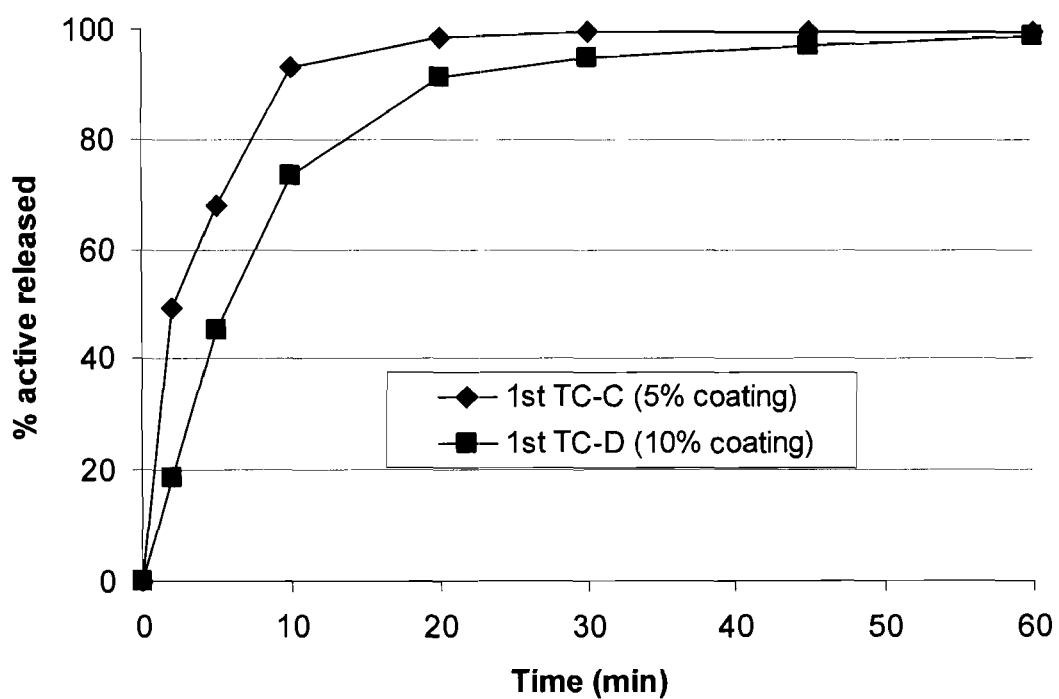

FIG 3. Release profiles of cellulose acetate or cellulose acetate/ethyl cellulose coated calcium formate
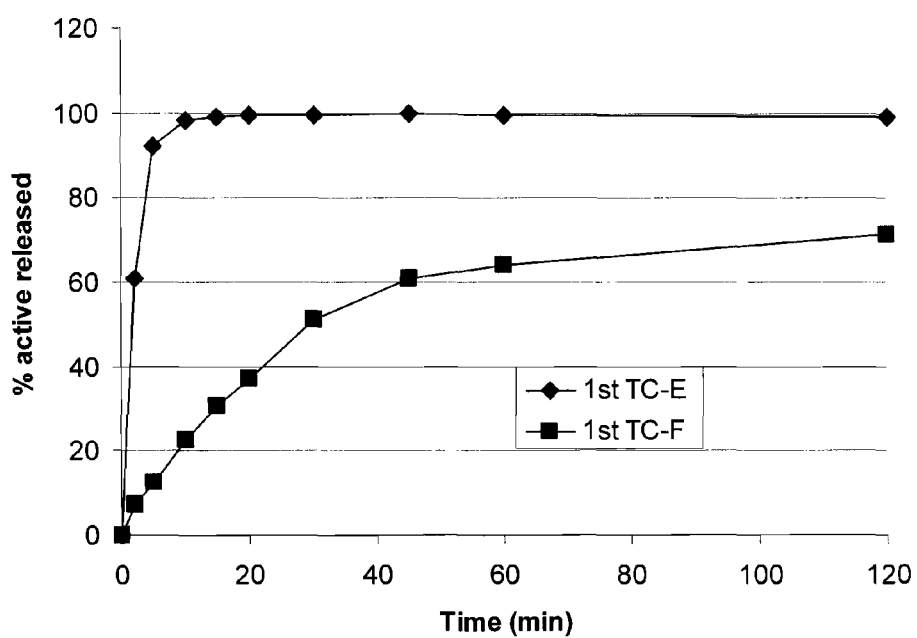

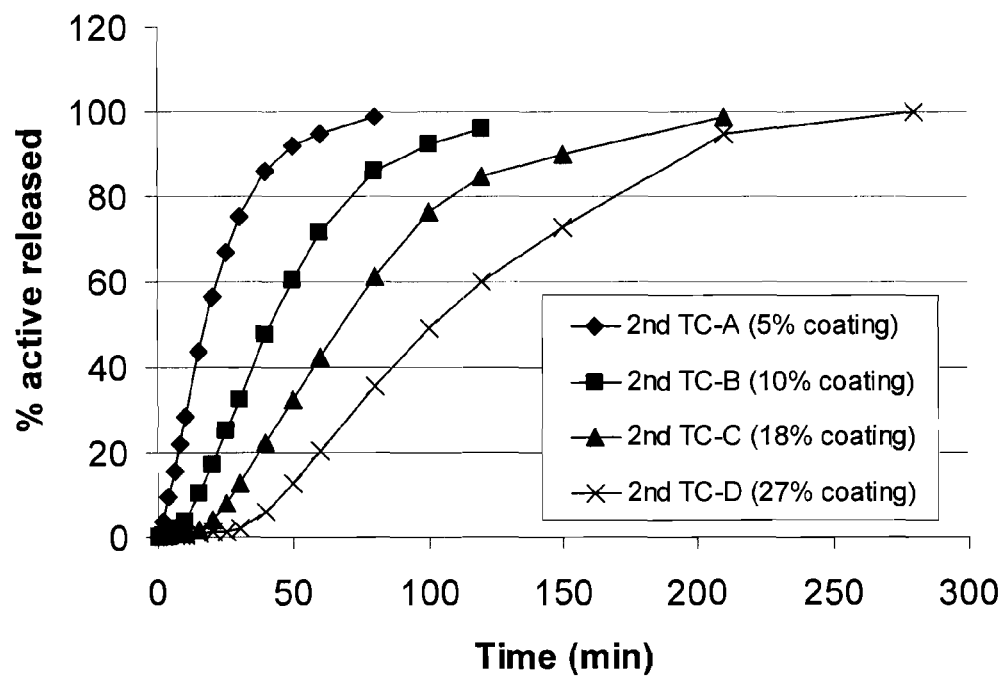
FIG 4. Release profiles of poly(meth)acrylate coated sodium carbonate

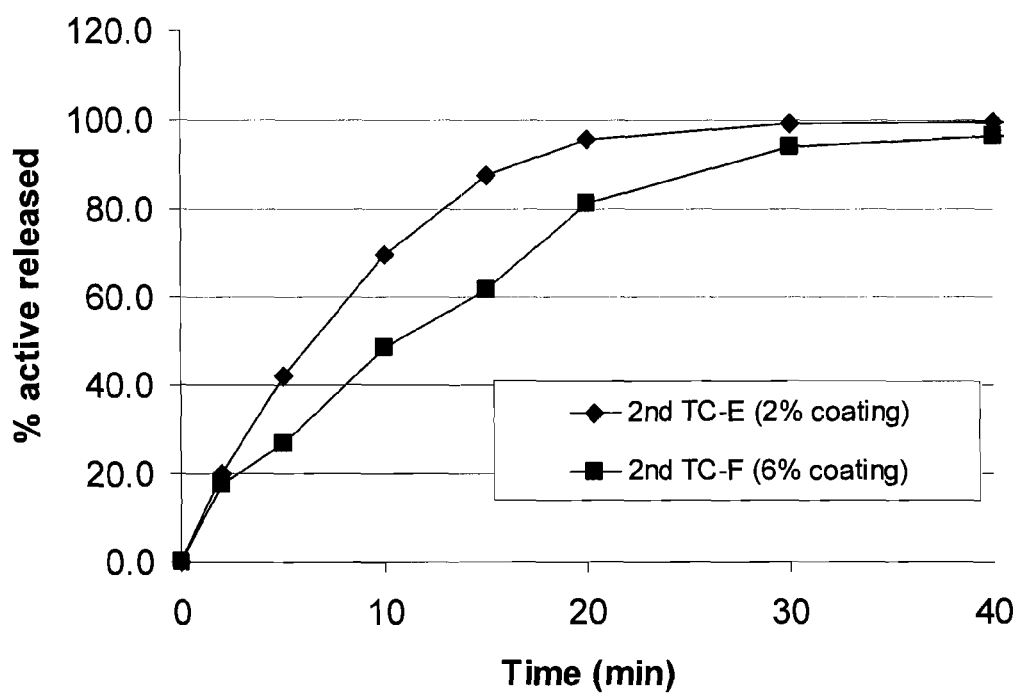
FIG 5. Release profiles of maleated polypropylene coated sodium carbonate FIG 6 is a graphical plot of swell/deswell curves for a specific SAP product with various blends of 1st triggering compositions;
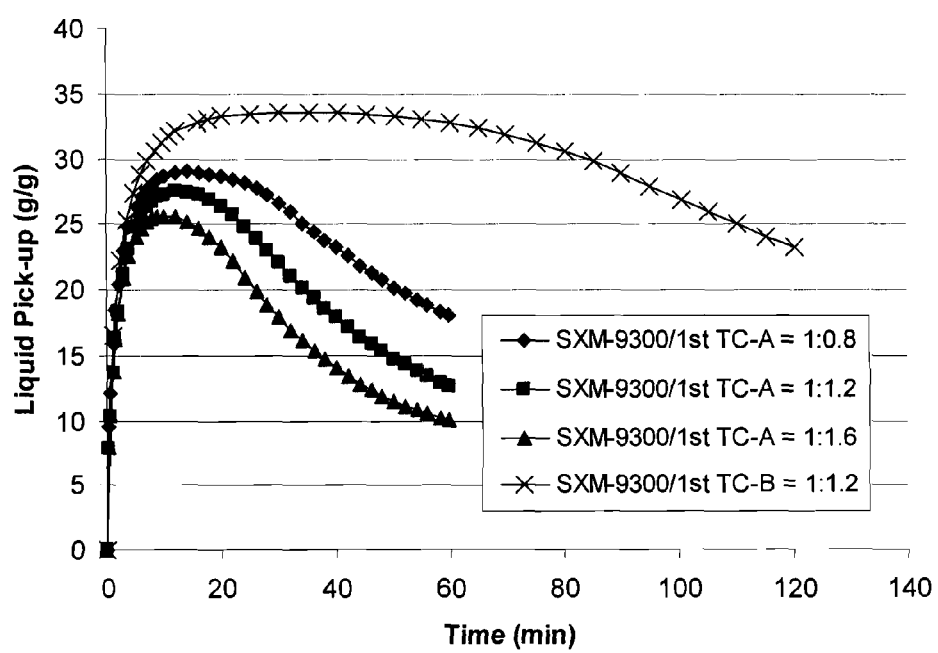

FIG 7. Swell/deswell/reswell curves for SXM-9300 and with various blends of 1$^{st}$ and 2$^{nd}$ triggering compositions
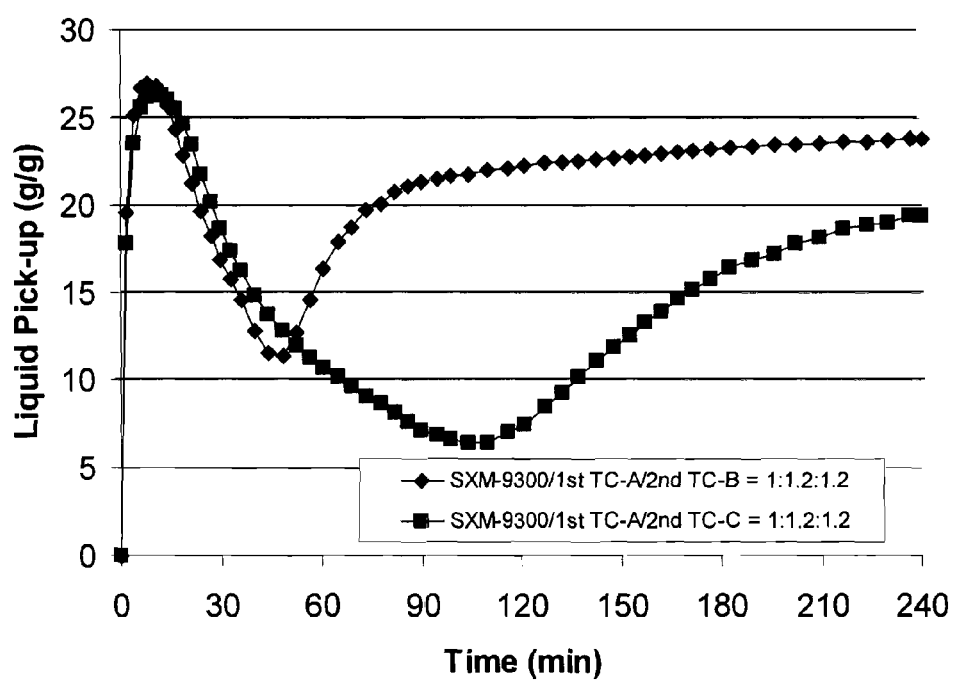

FIG 8. Swell/deswell/reswell curves for superabsorbent composition SAP-B and with triggering compositions 1$^{st}$ TC-A and 2$^{nd}$ TC-B
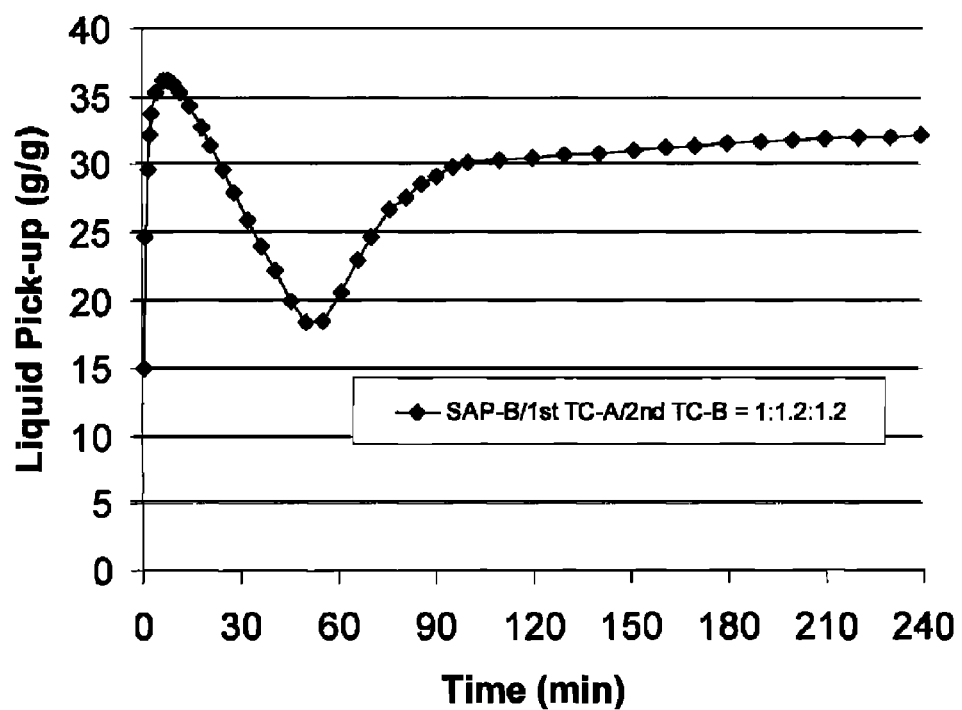

FIG 9. Swell/deswell/reswell curves for SAP-C and SAP-D and with various blends of triggering compositions 1st TC-A and 2nd TC-B
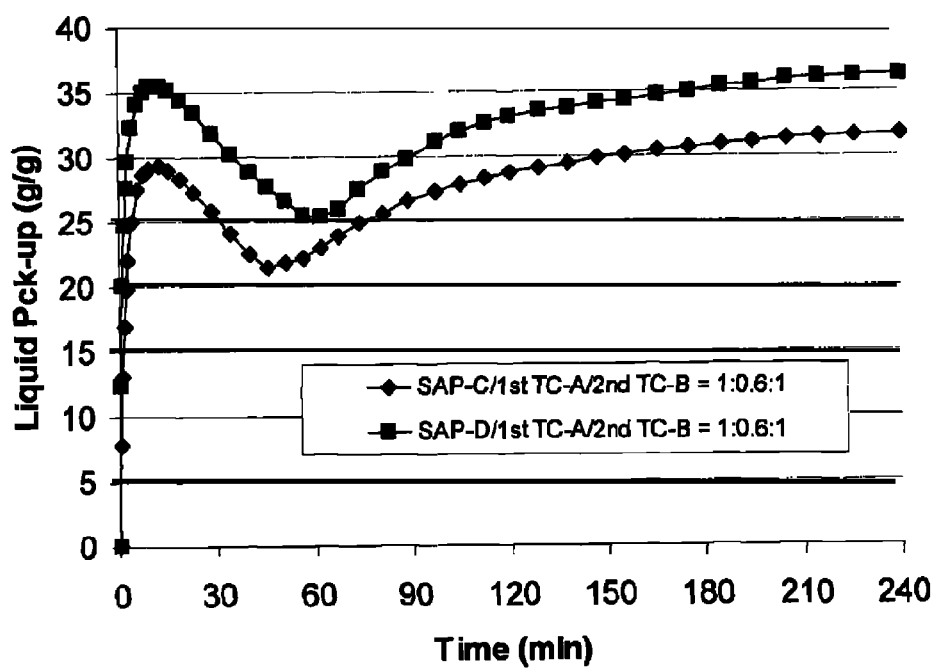

FIG 10. Swell/deswell/reswell curves for a specific commercial SAP product and with triggering compositions 1st TC-C and 2nd TC-A
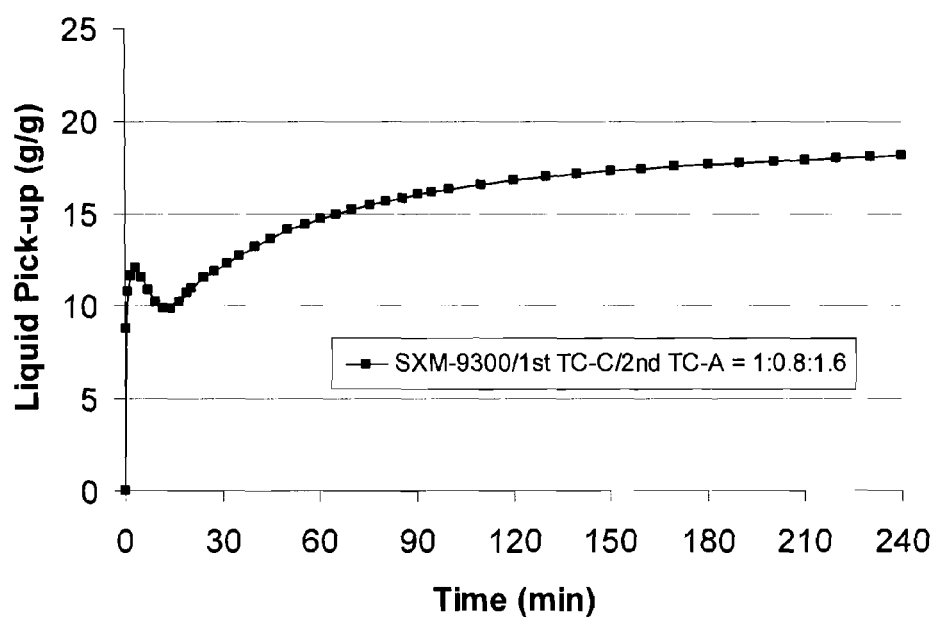

FIG 11. Swell/deswell/reswell curves for superabsorbent composition SAP-B and with various blends of 1st and 2nd triggering compositions
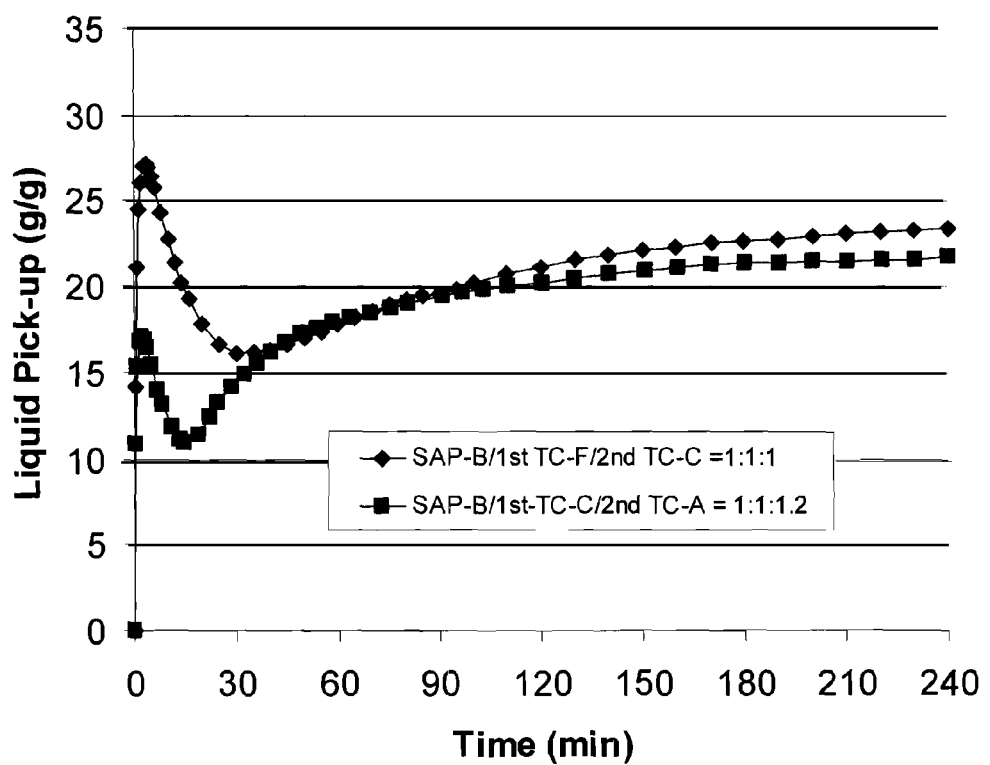

FIG 12. Swell/deswell/reswell curves for superabsorbent composition SAP-D and with various blends of triggering compositions $1^{st}$ TC-F and $2^{nd}$ TC-C
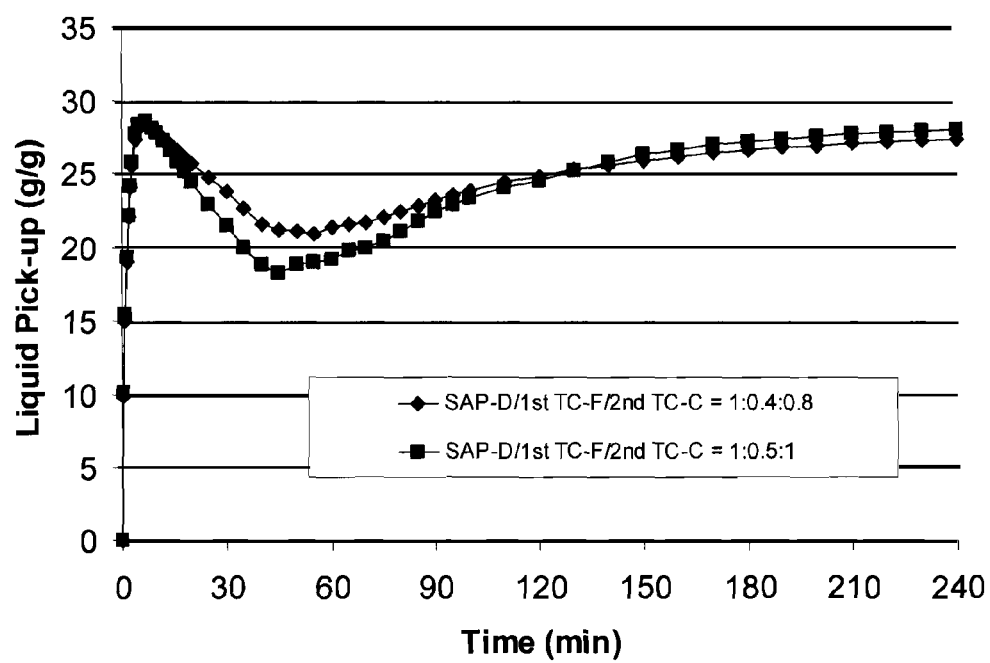

FIG 13. An apparatus for the Swell/Deswell/Reswell Test
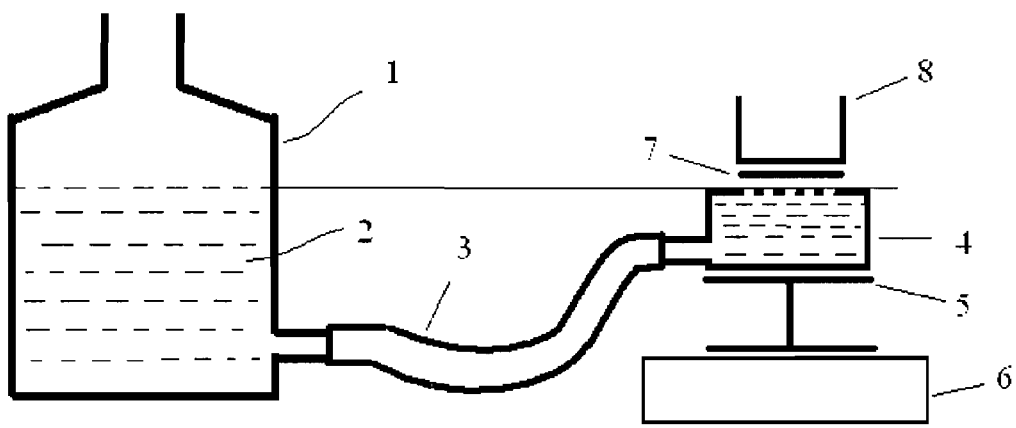

SUPERABSORBENT POLYMER COMPOSITIONS HAVING A TRIGGERING COMPOSITION

BACKGROUND

A superabsorbent polymer composition in general refers to a water-swellable, water-insoluble material capable of absorbing at least about 10 times its weight, and up to about 25 times or more of its weight in an aqueous solution containing 0.9 weight percent sodium chloride solution in water. The present invention relates to superabsorbent polymer compositions which absorb water, aqueous liquids, and blood.

A superabsorbent polymer is a crosslinked partially neutralized polymer that is capable of absorbing large amounts of aqueous liquids and body fluids, such as urine or blood, with swelling and the formation of hydrogels, and of retaining them under a certain pressure in accordance with the general definition of superabsorbent material. Superabsorbent polymer compositions may include post-treatment of the superabsorbent polymer such as surface crosslinking, surface treatment, and other treatment. Superabsorbent polymer particles are particles of superabsorbent polymers or superabsorbent polymer compositions. The acronym SAP may be used in place of superabsorbent polymer, superabsorbent polymer composition, and particles herein. A comprehensive survey of superabsorbent polymer compositions, and their use and manufacture, is given in F. L. Buchholz and A. T. Graham (editors) in "Modern Superabsorbent Polymer Technology," Wiley-VCH, New York, 1998.

Commercially available superabsorbent polymer compositions include crosslinked polyacrylic acids or crosslinked starch-acrylic acid graft polymers, in which some of the carboxyl groups are neutralized with sodium hydroxide solution or potassium hydroxide solution.

A primary use of superabsorbent polymer compositions is in absorbent composites that are used in sanitary articles, such as babies' diapers, incontinence products, or sanitary towels. For fit, comfort, and aesthetic reasons, and from environmental aspects, there is an increasing trend to make sanitary articles smaller and thinner. This is being accomplished by reducing the content of the high volume fluff fiber in these articles. To ensure a constant total retention capacity of body fluids in the sanitary articles, more superabsorbent polymer composition content is being used in these sanitary articles.

Fluid distribution in an absorbent composite is generally dependent on the amount of free liquid available for distribution, the structure and materials of the absorbent composite, and a time factor. However, current absorbent composites useful in absorbent cores of absorbent articles generally may have inadequate, or less than desirable, fluid distribution properties. Poor fluid distribution decreases the full utility efficiency of absorbent composites as not all of the superabsorbent polymer composition is absorbing liquid.

One potential solution known in the art for improving fluid distribution in an absorbent composite is to use superabsorbent polymer compositions having a slow absorbency rate. The theory for using slow absorbency superabsorbent polymer compositions is that there would be diminished or delayed gel blocking and thereby would provide more free liquid and time for the liquid to distribute away from the insult target area. However, although distribution may be enhanced using the slow superabsorbent, the absorbent composite typically does not provide necessary leakage protection.

As may be seen in the use of slow absorbency superabsorbent polymer compositions, there is a conflict between the functions of lockup and distribution. One problem is that the time required to lockup liquid into the superabsorbent polymer composition and open up composite structure by SAP swelling is relatively long. It is this free liquid which is in the target area during fluid insult period that is difficult to get into the absorbent product core and believed to be responsible for leakage of liquid from an absorbent product while in use. To reduce leakage, the superabsorbent polymer composition needs to lockup liquid at a rate similar to the liquid delivery rate so that an absorbent product has adequate fluid handling functionality. However, if the superabsorbent polymer compositions absorb the liquid, then distribution of liquid is reduced since there is no free liquid to be distributed after fluid insult. Using superabsorbent polymer compositions that have the ability to quickly lockup liquid and then gradually release this liquid so that it may be distributed will result in desirable leakage and distribution behavior.

There is a need for a superabsorbent polymer composition that allows enhanced fluid distribution properties while maintaining other absorbent properties, thereby maximizing the absorbent capabilities of superabsorbent polymer composition.

SUMMARY

This invention relates to an absorbent composition which utilizes multifunctional materials to enhance distribution of fluids. Current commercial superabsorbent polymer compositions function to swell and absorb fluids. This invention relates to the use of absorbent compositions which swell and absorb fluids, and which also may deswell and release fluids away from the swollen superabsorbent polymer composition, and which also may reswell and absorb fluids from an additional fluid insult.

The absorbent compositions of this invention comprise superabsorbent polymer compositions and triggering compositions. The triggering compositions of this invention comprise water-soluble chemicals which trigger superabsorbent polymers to deswell or reswell.

The superabsorbent polymer compositions of this invention swell during absorption of fluids and, in one embodiment, may be triggered to deswell and release fluid by a triggering composition. The free liquid released by the triggered deswelling may then be free to be distributed away from the swollen superabsorbent polymer composition where the initial insult occurred. The deswelled superabsorbent polymer compositions, in one embodiment, may be triggered to reswell and absorb fluid by a second triggering composition. The swelling-deswelling-reswelling cycle allows insult liquid to be locked up, released, distributed throughout an absorbent composite, and then be capable of reswelling on subsequent liquid insults, fully utilizing the absorbent capabilities of the full absorbent composite and minimizing leakage.

In another embodiment of this invention, a superabsorbent polymer composition may be triggered to deswell and reswell by a change in the solubility of the triggering chemicals. In one embodiment of this invention, an absorbent composition may comprise a superabsorbent polymer composition having anionic functional groups, a first triggering composition comprising a first water-soluble chemical comprising cations X having an ionized valence of two or more, and a second triggering composition comprising a second water-soluble chemical comprising anions Y, wherein the cations X of the first water-soluble chemical are capable of complexing with the anions Y of the second water-soluble chemical to form a salt having a solubility product constant $Ksp<10^{-5}$.

This invention further relates to triggering compositions having a selected release profile for release of the active agent from the triggering compositions, and a method for the preparation of such triggering compositions. Different absorbent applications, and/or triggering compositions, may require different types of release profiles such as a singular release profile or a sigmoidal release profile. In one embodiment, the release profile of the triggering compositions may be controlled by selecting appropriate coating polymers that are applied on the surface of the water-soluble chemicals. In another embodiment, the release profile may also be controlled by adjusting the coating process for applying the coating polymers.

This invention further relates to absorbent compositions demonstrating swelling-deswelling-reswelling behavior and to a method of controlling the timing of the swelling-deswelling-reswelling cycle. An embodiment of this invention is an absorbent composition comprising a superabsorbent polymer composition, a first triggering composition having a selected release profile for releasing the first water-soluble solid chemical, and a second triggering composition having a release profile for releasing the second water-soluble solid chemical from the second triggering composition, wherein the first water-soluble chemical has higher cumulative release than the second water-soluble chemical after exposure to aqueous fluid and before the first water-soluble chemical is about 100% released. The timing for absorbing/releasing fluid may be controlled by selecting suitable release profiles for the first and second triggering compositions, and/or by adjusting the release rates of the first and second triggering compositions, and/or by altering the absorption rate of the superabsorbent polymer composition, and/or by altering the mixing ratio of the superabsorbent polymer composition, the first triggering composition, and the second triggering composition. The acronym $1^{st}$ TC and $2^{nd}$ TC may be used in place of first triggering composition and second triggering composition respectively herein.

An additional embodiment of this invention relates to superabsorbent polymer compositions having improved absorption capacity efficiency and mass efficiency in the swelling-deswelling-reswelling cycle. The absorption capacity efficiency improvement generally refers to the increase of the swelling or reswelling capacity of an absorbent composition compared with the absorbent composition comprising a commercial superabsorbent polymer composition. The mass efficiency improvement refers to the utilization of a lesser percentage of deswell triggering composition with respect to the superabsorbent polymer while achieving the same amount of deswelling liquid. Mass efficiency improvement also refers to the utilization of a lesser percentage of reswell triggering composition with respect to superabsorbent polymer while achieving the same amount of reswelling capacity. The capacity efficiency improvement may be achieved by adjusting the degree of neutralization and crosslinking of superabsorbent polymer compositions, and/or by altering the absorption speed of superabsorbent polymer compositions, and/or by altering the mixing ratio of the superabsorbent polymer composition, the first triggering composition, and the second triggering composition. The mass efficiency improvement may also be achieved in the same manner.

Numerous other embodiments, features, and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects, and advantages of the present invention will become better understood with regard to the following description, appended claims, and accompanying drawings where:

FIG. 1 is a graphical plot of release profiles of poly(meth) acrylate coated sulfamic acid;

FIG. 2 is a graphical plot of release profiles of poly(meth) acrylate coated calcium formate;

FIG. 3 is a graphical plot of release profiles of cellulose acetate and cellulose acetate/ethyl cellulose coated calcium formate;

FIG. 4 is a graphical plot of release profiles of poly(meth) acrylate coated sodium carbonate;

FIG. 5 is a graphical plot of release profiles of maleated polypropylene coated sodium carbonate;

FIG. 6 is a graphical plot of swell/deswell curves for a specific SAP product with various blends of $1^{st}$ triggering compositions;

FIG. 7 is a graphical plot of swell/deswell/reswell curves for a specific SAP product and with various blends of $1^{st}$ and $2^{nd}$ triggering compositions;

FIG. 8 is a graphical plot of swell/deswell/reswell curves for superabsorbent composition SAP-B and with triggering compositions $1^{st}$ TC-A and $2^{nd}$ TC-B;

FIG. 9 is a graphical plot of swell/deswell/reswell curves for SAP-C and SAP-D and with various blends of triggering compositions $1^{st}$ TC-A and $2^{nd}$ TC-B;

FIG. 10 is a graphical plot of swell/deswell/reswell curves for a specific SAP product and with triggering compositions $1^{st}$ TC-C and $2^{nd}$ TC-A;

FIG. 11 is a graphical plot of swell/deswell/reswell curves for superabsorbent composition SAP-B and with various blends of $1^{st}$ and $2^{nd}$ triggering compositions;

FIG. 12 is a graphical plot of swell/deswell/reswell curves for superabsorbent composition SAP-D and with various blends of triggering compositions $1^{st}$ TC-F and $2^{nd}$ TC-C; and FIG. 13 is an apparatus for the Swell/Deswell/Reswell Test.

DEFINITIONS

It should be noted that when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices that may absorb and contain fluids. For example, personal care absorbent articles refer to devices that are placed against or near the skin to absorb and contain the various fluids discharged from the body.

The term "absorbent composite" is used herein to refer to a mixture of superabsorbent polymer composition or absorbent composition with other components including, but not limited to, fibers, foams, nonwovens, films, or other carrier materials.

The term "absorbent composition" refers to a combination of superabsorbent polymer composition and at least one triggering composition.

The term "coating" is used herein to mean a layer of any substance spread over a surface. The term "complexing" is used herein to describe the forming of molecules by the combination of ligands (such as anions) and metal ions.

The term "crosslinked" used in reference to the superabsorbent polymer refers to any means for effectively rendering normally water-soluble materials substantially water-insoluble but swellable. Such a crosslinking means may include, for example, physical entanglement, crystalline domains, covalent bonds, ionic complexes and associations, hydrophilic associations such as hydrogen bonding, hydrophobic associations, or Van der Waals forces.

The term "desorb" is used herein to mean to release fluids from the superabsorbent polymer composition.

The term "deswell" is used herein to refer to the decrease in size of the superabsorbent polymer composition that occurs while fluids are being desorbed from the superabsorbent polymer composition.

The term "disposable" is used herein to describe absorbent articles that are not intended to be laundered or otherwise restored or reused as an absorbent article after a single use. Examples of such disposable absorbent articles include, but are not limited to, personal care absorbent articles, health/medical absorbent articles, and household/industrial absorbent articles.

The term "dry superabsorbent polymer composition" generally refers to the superabsorbent polymer composition having less than about 10% moisture.

The term "multivalent ions" is used herein to mean an electrically charged atom or group of atoms formed by the loss or gain of multiple electrons, as a cation (positive ion), which is created by a loss of one or more electrons, or as an anion (negative ion), which is created by a gain of one or more electrons.

The terms "particle," "particulate," and the like, when used with the term "superabsorbent polymer," refer to the form of discrete units. The units may comprise flakes, fibers, agglomerates, granules, powders, spheres, pulverized materials, or the like, as well as combinations thereof. The particles may have any desired shape: for example, cubic, rod-like, polyhedral, spherical or semi-spherical, rounded or semi-rounded, angular, irregular, et cetera. Shapes having a high aspect ratio, like needles, flakes, and fibers, are also contemplated for inclusion herein. The terms "particle" or "particulate" may also include an agglomeration comprising more than one individual particle, particulate, or the like. Additionally, a particle, particulate, or any desired agglomeration thereof may be composed of more than one type of material.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

The term "polyolefin" as used herein generally includes, but is not limited to, materials such as polyethylene, polypropylene, polyisobutylene, polystyrene, ethylene vinyl acetate copolymer, and the like, the homopolymers, copolymers, terpolymers, etc., thereof, and blends and modifications thereof.

The term "polyolefin" shall include all possible structures thereof, which include, but are not limited to, isotatic, synodiotactic, and random symmetries. Copolymers include atactic and block copolymers.

The term "release profile" as used herein refers to the quantity or amount of active agent that is released into solution from the triggering compositions as a function of time, that are typically illustrated as the cumulative release, expressed as a percentage of the total amount of active agent present in the triggering composition, as a function of time and may be shown as a graphical summary of the releasing of the agent into solution of a particular substance.

The term "reswell" is used herein to refer to the growth in size of the superabsorbent polymer composition that occurs while fluids are being absorbed by the superabsorbent polymer composition after deswell.

The term "singular release profile" refers to a release profile that is represented by a concave downward curve. The initial release rate is fast but gradually becomes slower.

The term "sigmoidal release profile" refers to a release profile that is represented by a concave upward then concave downward curve. It is generally characterized by an initial lag phase, a steep intermediate release phase, and a slow final release phase.

The term "solubility product constant" is a simplified equilibrium constant (Ksp) defined for equilibrium between a solid and its respective ions in a solution. Its value indicates the degree to which a compound dissociates in water. The higher the solubility product constant, the more soluble the compound. The Ksp expression for a salt is the product of the concentrations of the ions, with each concentration raised to a power equal to the coefficient of that ion in the balanced equation for the solubility equilibrium.

The term "superabsorbent materials" refers to water-swellable, water-insoluble organic or inorganic materials including superabsorbent polymers and superabsorbent polymer compositions capable, under the most favorable conditions, of absorbing at least about 10 times their weight, or at least about 15 times their weight, or at least about 25 times their weight in an aqueous solution containing 0.9 weight percent sodium chloride.

The term "superabsorbent polymer composition" refers to a superabsorbent polymer comprising a surface additive in accordance with the present invention.

The terms "superabsorbent polymer" and "superabsorbent polymer preproduct" refer to a material that is produced by conducting all of the steps for making a superabsorbent polymer as described herein, up to and including drying the material, and coarse grinding in a crusher.

The term "surface crosslinking" means that the level of functional crosslinks in the vicinity of the surface of the superabsorbent polymer particle generally is higher than the level of functional crosslinks in the interior of the superabsorbent polymer particle. As used herein, "surface" describes the outer-facing boundaries of the particle. For porous superabsorbent polymer particles, exposed internal surfaces also are included in the definition of surface.

The term "swell" is used herein to refer to the growth in size of the superabsorbent polymer composition that occurs while fluids are being absorbed by the superabsorbent polymer composition.

The term "thermoplastic" describes a material that softens when exposed to heat and which substantially returns to a non-softened condition when cooled to room temperature.

The term "triggering composition" is used herein to refer to a material that includes a chemical that when released causes the superabsorbent polymer composition to deswell or to reswell as required.

The term "% by weight" or "% wt," when used herein and referring to components of the superabsorbent polymer composition, is to be interpreted as based on the weight of the dry superabsorbent polymer composition, unless otherwise specified herein.

These terms may be defined with additional language in the remaining portions of the specification.

DETAILED DESCRIPTION

The absorbent compositions according to the present invention have the property that they rapidly absorb large amounts of urine or other body fluids and may be employed in many products such as sanitary towels, diapers, or wound coverings. Since the absorbent compositions according to the invention have the ability to quickly lockup liquid and then gradually release this liquid so that the liquid may be distributed throughout the absorbent composites, they may result in higher utility efficiency of absorbent composites, so that they are more desirably employed in thinner articles with reduced basis weight, or highly shaped absorbent composites with narrow crotch for better fit, when compared to conventional current absorbent products. Such absorbent composites may also be suitable for use as a homogeneous superabsorber layer without fluff content within the diaper construction, resulting in the possibility of thinner hygiene articles.

The absorbent compositions of the present invention may also be employed in absorbent articles that are suitable for further uses. In particular, the absorbent compositions of this invention may be used in absorbent composites for absorbent products for water or aqueous liquids, desirably in constructions for absorption of body fluids, in foamed and non-foamed sheet-like structures, in packaging materials, in constructions for plant growing, as soil improvement agents, or as active compound carriers. For this, they are processed into a web by mixing with paper or fluff or synthetic fibers or by distributing the absorbent composition particles between substrates of paper, fluff, or non-woven textiles, or by processing into carrier materials. They are further suited for use in absorbent composites such as wound dressings, packaging, agricultural absorbents, food trays and pads, and the like.

In one embodiment of this invention, the superabsorbent polymer composition is capable of swelling and absorbing fluids and, when a triggering composition is applied, deswelling and releasing fluids, and when a second triggering composition is applied, reswelling and absorbing fluids again may occur. "Swelling" refers to the growth in size of the superabsorbent polymer composition that occurs while fluids are being absorbed by the superabsorbent polymer composition. For swelling to occur in superabsorbent polymer compositions, fluids must be absorbed; therefore, to say that a superabsorbent polymer composition is swelling also means the superabsorbent polymer composition is absorbing liquid. "Deswelling" refers to the decrease in size of the superabsorbent polymer composition that occurs while fluids are being desorbed from the superabsorbent polymer composition. For deswelling to occur in a superabsorbent polymer composition, the absorbed fluids must be desorbed, or released from the superabsorbent polymer composition; therefore, to say a superabsorbent polymer composition is deswelling also means the superabsorbent polymer composition is releasing liquid. "Reswelling" refers to the increase in size of the superabsorbent polymer composition that occurs while fluids are being absorbed by the superabsorbent polymer composition after deswell.

Superabsorbent polymer compositions of this invention are capable of deswelling and desorbing fluids after a triggering composition is applied. In one embodiment of this invention, a triggering composition functions after the superabsorbent polymer compositions are saturated, or substantially saturated, with absorbed liquid. The triggering composition may cause the superabsorbent polymer composition to deswell and release the absorbed liquid.

The absorbent composition of may include the superabsorbent polymer composition and the first and second triggering compositions have a particle size from about 150 μm to about 850μm and wherein when the absorbent composition is contacted with a fluid that causes the superabsorbent polymer composition to absorb the fluid to form a swollen superabsorbent polymer composition, and the first triggering composition is combined with the swollen superabsorbent polymer results in the swollen superabsorbent polymer composition deswelling a portion of the fluid from the swollen superabsorbent polymer composition, and the resulting deswelled swollen superabsorbent polymer composition has a second absorption capacity that is about 20% or more less than the first absorption capacity; and wherein when the second triggering composition contacts the combination of the swollen superabsorbent polymer composition and first triggering composition of b) the resulting superabsorbent polymer composition has a third absorption capacity that is greater than the second absorption capacity.

The superabsorbent polymer composition and the triggering composition may be present in the absorbent composition in a weight ratio from about 1:0.01 to about 1:10, or from about 1:0.1 to about 1:2. The absorbent composition may include from about 10 to about 90 wt % of superabsorbent polymer composition, from about 5 to about 60 wt % of a first triggering composition, and from about 5 to about 60 wt % of a second triggering composition.

The triggering composition as described herein may be of a size that, when incorporated into a personal care product such as a baby diaper, they cannot readily migrate out of the composite product. Generally, the triggering compositions may have a particle size of from about 5 μm to about 1000 μm, or from about 50 μm to about 1000 μm, or from about 100 μm to about 850 μm, or from about 150 μm to about 850 μm.

Triggering compositions may be applied to the absorbent composite by means of blending, encapsulation, coating, attaching using a binder material, printing, laminating, strategically blending, and/or placing in specific pockets of the composites, combinations of these, or other means. Triggering compositions may have time delayed effects, and only start to function when such effects are eliminated.

In another embodiment of this invention, at least one of said triggering compositions is spatially separated from said superabsorbent polymer composition.

The superabsorbent polymer compositions of this invention swell during absorption of fluids and, in one embodiment, may be triggered to deswell and release fluid by the first triggering composition. The deswelled superabsorbent polymer compositions may also be triggered to reswell and absorb fluid by a second triggering composition. The swelling-deswelling-reswelling cycle may be repeated multiple times.

In another embodiment of this invention, a superabsorbent polymer composition may be triggered to deswell and reswell by a change in the solubility of the triggering composition chemicals. In one embodiment of this invention, an absorbent composition may comprise a superabsorbent polymer composition having anionic functional groups; a first triggering composition comprising a first water-soluble chemical comprising cations X having an ionized valence of two or more; and a second triggering composition comprising a second water-soluble chemical comprising anions Y, wherein the cations X of the first water-soluble chemical are capable of complexing with the anions Y of the second water-soluble chemical to form a salt having a solubility product constant $Ksp<10^{-5}$. Without intending to be bound thereby, it is hypothesized that the ion exchange reaction between the first triggering composition and the superabsorbent polymers may result into ionic crosslinking in the gel network that triggers the superabsorbent polymers to deswell and release the absorbed liquid. The ion exchange reaction between the second triggering composition and the deswelled superabsorbent polymers may remove at least a portion of ionic crosslinking so that the superabsorbent polymer may reswell and absorb additional liquid.

The first water-soluble chemical as described herein comprises cations having an ionized valence of two or more. Specific examples of the first chemical include, for example, aluminum chloride, aluminum sulfate, barium chloride, calcium acetate, calcium chloride, calcium formate, magnesium acetate, magnesium chloride, magnesium formate, zinc acetate, zinc chloride, zinc formate, and zinc sulfate.

The water-soluble chemical of the second triggering composition as described herein includes anions which are capable of forming an insoluble salt with the cations of the first triggering composition. The anions may be selected from $F^-$, $HCO_3^-$, $CO_3^{2-}$, $PO_4^{3-}$, $SO_4^{2-}$, oxalate, citrate, sulfide, and polyphosphate anions. Specific examples of this chemical include, for example, sodium fluoride, sodium hydrogen carbonate, sodium carbonate, sodium citrate, sodium oxalate, sodium phosphate, sodium polyphosphate, sodium sulfide, sodium sulfate, or sodium tripolyphosphate.

The triggering compositions as described herein may further comprise a polymeric coating material for achieving controlled release of water-soluble chemicals. Specific examples of the coating material include, for example, poly(meth)acrylate copolymers, polyacrylate copolymers, ethyl cellulose, sodium carboxymethylcellulose, cellulose acetate, polyethylene glycol, maleated polypropylene, polyolefin copolymers, or combinations thereof. In certain preferred embodiments, the polymeric coating used in the coatings of the present invention comprises copolymerizates of acrylic and methacrylic acid esters with a low content of quaternary ammonium groups. Such copolymerizates are often referred to as ammonio methacrylate copolymers, and are commercially available from Rohm Pharma AG, e.g., under the tradename EUDRAGIT®. In certain embodiments, the polymeric coating used in the coatings of the present invention comprises ethyl cellulose and/or cellulose acetate. In other embodiments, the polymeric coating used in the coatings of the present invention may comprise maleated polypropylene.

In another embodiment, the absorbent composition may include a first and second triggering compositions having a selected release profile respectively for releasing the water-soluble chemical after exposure to aqueous fluids, wherein the first water-soluble chemical has higher cumulative release than the second water-soluble chemical before the first water-soluble chemical is 100% released. The release profile is selected from singular release profile or sigmoidal release profile.

In another embodiment, the absorbent composition may include a first and second triggering compositions each having a release profile wherein from about 50 wt % to 100 wt % of the water-soluble solid chemical is released from the first or second triggering composition in less than about 240 minutes after exposure to aqueous liquid, as measured by the release profile measurement in Test Procedure as set forth hereafter.

In another embodiment, the absorbent composition may include a superabsorbent polymer composition comprising partially neutralized crosslinked poly(acrylic acid), having from about 40 to about 60 molar percent of the neutralized acidic functional groups, and a centrifuge retention capacity of at least about 15 grams of 0.9% by weight sodium chloride solution per gram of superabsorbent (g/g), or at least about 25g/g, or at least about 30g/g, or from about 25g/g to about 60g/g, as set forth by the Centrifuge Retention Capacity test set forth herein.

In another embodiment, the absorbent composition may include a superabsorbent polymer composition that may include from about 0.05 to about 10.0 wt % of a blowing agent. The blowing agent may be encapsulated by a resin that may be selected from natural or synthetic resins, acrylonitrile-butadiene rubbers, viscous settable ceramic materials, polyolefins, polyethylene glycol, olefin copolymers, polyaromatic olefins, styrenic compounds or polymerized halo-diolefins. In another embodiment, the absorbent composition may include a superabsorbent polymer composition that has a vortex time of 45 seconds or less as measured by the Vortex Test set forth hereafter. It has been discovered that the increase of absorption speed of the superabsorbent polymer described herein may improve the swelling and reswelling capacity in the swelling-deswelling-reswelling cycle.

In another embodiment of this invention, it has been discovered that the mass efficiency and absorption capacity efficiency may be improved by the decrease of degree of neutralization and decrease of internal crosslinking of superabsorbent polymers. In another embodiment of this invention, a superabsorbent polymer composition may have a degree of neutralization lower than 70% degree of neutralization. In particular, the absorbent composition comprises a superabsorbent polymer composition comprising partially neutralized crosslinked poly(acrylic acid) wherein from about 40 molar percent to about 60 molar percent of the acidic functional groups are neutralized, and having a pH less than about 6.0, a first triggering composition that includes a first water-soluble chemical, and a second triggering composition having a pH of about 10 or more wherein the absorbent composition exhibits a swell-deswell-reswell behavior and the resultant swollen superabsorbent polymer composition has a pH higher than the original superabsorbent polymer composition. The superabsorbent polymers as described herein are more sensitive to the triggering compositions. In another embodiment, the first triggering composition comprises an acid such as sulfamic acid (also known as amidosulfonic acid, amidosulfuric acid, aminosulfonic acid, and sulfamidic acid) or a water-soluble chemical having multivalent cations such as $Ca^{2+}$, and the second triggering composition comprises a base or a basic material such as sodium carbonate. One advantage of this invention is that a lesser percentage of the first and second triggering compositions with respect to the superabsorbent polymer can be utilized to achieve the same amount of deswelling liquid and reswelling capacity. In addition, the absorbent composition as described herein shows an increase of the swelling and reswelling capacities compared with the absorbent composition comprising a commercial superabsorbent polymer.

In another embodiment of this invention, the superabsorbent polymer composition and the first and second triggering compositions are in particle form, and the superabsorbent polymer composition particles and the first and second triggering composition particles have a particle size from about 150 μm to about 850 μm as measured by screening through a U.S. standard 20 mesh screen and retained on a U.S. standard 100 mesh screen.

In another embodiment of this invention, the absorbent composition comprises a superabsorbent polymer composition comprising a blowing agent; a first triggering composition comprising a first water-soluble solid chemical wherein the first triggering composition has a release profile for releasing the water-soluble solid chemical from the triggering composition wherein the release profile is selected from a singular release profile or a sigmoidal release profile; and a second triggering composition comprising a second water-soluble solid chemical wherein the second triggering composition has a sigmoidal release profile for releasing the second water-soluble solid chemical from the triggering composition, wherein the first water-soluble chemical has higher cumulative release than the second water-soluble chemical after exposure to aqueous fluid and before about 100% release.

In another embodiment of this invention, an absorbent composition comprises a superabsorbent polymer composition comprising partially neutralized crosslinked poly(acrylic acid) and having a first absorption capacity; a first triggering composition; and a second triggering composition, wherein the superabsorbent polymer composition and the first and second triggering compositions are in particle form, and the superabsorbent polymer composition particles and the first and second triggering composition particles have a particle size of from more than about 150 μm to less than about 1000 μm.

In another embodiment of this invention, an absorbent composition comprises a superabsorbent polymer composition; and a triggering composition comprising a water-soluble solid chemical wherein the triggering composition has a release profile for releasing the water-soluble solid chemical from the triggering composition, wherein the release profile is selected from a singular release profile or a sigmoidal release profile, wherein the superabsorbent polymer composition and the triggering composition are in particle form, and the superabsorbent polymer composition particles and the triggering composition particles have a particle size of from more than about 150 μm to less than about 1000 μm.

The water-soluble solid chemical as described herein is selected from sulfamic acid, citric acid, calcium formate, calcium chloride, calcium hydroxide, calcium oxide, calcium acetate, magnesium acetate, magnesium chloride, magnesium formate, barium chloride, aluminum chloride, aluminum sulfate, sodium aluminate, zinc chloride, zinc acetate, zinc formate, zinc sulfate, sodium fluoride, sodium hydrogen carbonate, sodium carbonate, sodium sulfate, sodium phosphate, sodium polyphosphate, sodium oxalate, sodium sulfide, or sodium tripolyphosphate.

In another embodiment of this invention, an absorbent composition comprises a superabsorbent polymer composition; a first triggering composition comprising a first water-soluble solid chemical wherein the first triggering composition may have a release profile for releasing the water-soluble solid chemical from the triggering composition, wherein the release profile is selected from a singular release profile or a sigmoidal release profile; and a second triggering composition comprising a second water-soluble solid chemical wherein the second triggering composition has a release profile for releasing the second water-soluble solid chemical from the triggering composition, wherein the release profile is selected from a singular release profile or a sigmoidal release profile; wherein the first water-soluble chemical has higher cumulative release than the second water-soluble chemical after exposure to aqueous fluid and before about 100% release.

An advantage of the absorbent compositions of the present invention is that the timing in swelling-deswelling-reswelling cycle may be controlled by adjusting such parameters as the absorption rate of the superabsorbent polymer composition, the release rate of the first and second triggering compositions, and the mixing ratio of the superabsorbent polymer composition and triggering compositions.

This invention further relates to triggering composition comprising a water-soluble solid chemical; and a polymeric coating material that coats the water soluble chemical in the amount of from about 0.1 wt % to about 50 wt % of said water-soluble chemical, and wherein the triggering composition has a singular or sigmoidal release profile for releasing the water-soluble solid chemical from the triggering composition as measured by the release profile measurement in Test Procedure and wherein the triggering composition is in particle form, and has a particle size of less than about 1000 μm.

In another embodiment of this invention, the triggering composition comprises a water-soluble solid chemical selected from sulfamic acid, citric acid, aluminum chloride, aluminum sulfate, barium chloride, calcium acetate, calcium chloride, calcium formate, magnesium acetate, magnesium chloride, magnesium formate, zinc acetate, zinc chloride, zinc formate, zinc sulfate, sodium fluoride, sodium hydrogen carbonate, sodium carbonate, sodium citrate, sodium oxalate, sodium phosphate, sodium polyphosphate, sodium sulfide, sodium sulfate, or sodium tripolyphosphate, wherein said water-soluble solid chemical is coated with a polymeric coating selected from poly(meth)acrylate copolymers, polyacrylate copolymers, maleated polypropylene, ethyl cellulose, sodium carboxymethylcellulose, cellulose acetate, polyethylene glycol, polyolefin copolymers, or a combination thereof, and wherein the triggering composition has a singular or sigmoidal release profile for releasing the water-soluble solid chemical from the triggering composition as measured by the release profile measurement in Test Procedure and wherein the triggering composition is in particle form, and has a particle size of from more than about 150 μm to less than about 1000 μm.

Another embodiment of this invention includes a triggering composition comprising
   a. a water-soluble solid chemical; and
   b. a polymeric coating material that coats the water soluble chemical in the amount of from about 0.1 wt % to about 50 wt % of said water-soluble chemical; and
wherein the triggering composition has a release profile for releasing the water-soluble solid chemical from the triggering composition after exposure to an aqueous solution of the triggering composition, wherein the release profile is selected from a singular release profile or a sigmoidal release profile.

In another embodiment of this invention, from about 50 wt % to 100 wt % of the water-soluble solid chemical is released from the triggering composition in less than about 240 minutes after the initial insult.

In another embodiment of this invention, a triggering composition comprises a water soluble solid chemical selected from sulfamic acid, calcium formate, sodium fluoride, sodium hydrogen carbonate, sodium carbonate, citric acid, calcium chloride, calcium hydroxide, calcium oxide, magnesium chloride, magnesium formate, barium chloride, aluminum sulfate, sodium aluminate, sodium sulfate, sodium phosphate, sodium polyphosphate, sodium oxalate, sodium sulfide, or sodium tripolyphosphate; said water-soluble solid chemical is coated with a polymeric coating selected from poly(meth)acrylate copolymers, polyacrylate copolymers, maleated polypropylene, ethyl cellulose, sodium carboxymethylcellulose, cellulose acetate, polyethylene glycol, polyolefin copolymers, or a combination thereof. In certain embodiments, the polymeric coating used in the coatings of the present invention comprises copolymerizates of acrylic and methacrylic acid esters with a low content of quaternary ammonium groups. Such copolymerizates are often referred to as ammonio methacrylate copolymers, and are commercially available from Rohm Pharma AG, e.g., under the tradename EUDRAGIT®. In certain embodiments of the present invention, the acrylic coating is derived from a mixture of two acrylic resin lacquers used in the form of aqueous dispersions, commercially available from Rohm Pharma under the Tradename EUDRAGIT®RL 30 D and EUDRAGIT®RS 30 D, respectively. EUDRAGIT®RL 30 D and EUDRAGIT®RS 30 D are copolymers of acrylic and methacrylic esters with a low content of quaternary ammonium groups, the molar ratio of ammonium groups to the remaining neutral (meth)acrylic esters being 1:20 in EUDRAGIT ®RL 30 D and 1:40 in EUDRAGIT ®RS 30 D. The mean molecular weight is about 150,000.

Various embodiments of the present invention include a triggering composition, or a form thereof such as a first triggering composition or a second triggering composition, comprising a water-soluble solid chemical and a polymeric coating material that coats the water soluble chemical in the amount of from about 0.1 wt % to about 50 wt %, or amounts between these two limits, of said water-soluble chemical, wherein the triggering composition may have a release profile for releasing the water-soluble solid chemical from the triggering composition after an insult of an aqueous solution of the triggering composition, wherein the release profile is selected from a singular release profile or a sigmoidal release profile.

This invention further relates to triggering compositions having a selected release profile for release of the active agent from the triggering compositions, and to a method for the preparation of such triggering compositions. In one embodiment, the release profile of the triggering compositions can be controlled by selecting appropriate coating polymers that are applied on the surface of the water-soluble chemicals. In another embodiment, the release profile can be controlled by adjusting the coating process for applying the coating polymers.

The triggering composition(s) according to the present invention may be prepared by various methods known to those skilled in the art of preparing coated controlled release compositions. The triggering composition may be prepared continuously or discontinuously in laboratory or in a large-scale industrial manner.

An embodiment of a first method to prepare triggering composition(s) may include the following steps:
 a. providing the water-soluble solid chemical particles;
 b. placing the water-soluble chemical into a container;
 c. fluidizing the water-soluble solid chemical particles;
 d. spraying a polymeric coating onto the fluidized particles; and
 e. drying the coated particles, for example at about 50° C. for about 2 days.

A second method to prepare triggering compositions may include the following steps:
 a. stirring the water-soluble solid chemical particles in a mixer;
 b. adding polymeric coating to the water-soluble solid chemical particles; and
 c. heating the coated particles, for example at about 50° C. for about 2 hours.

A third method to prepare triggering compositions is a fluid bed process and may include the following steps:
 a. prepare a coating solution of the polymeric coating, talc, and triethyl citrate;
 b. fluidizing water-soluble solid chemical particles;
 c. spraying the coating solution onto the water-soluble solid chemical particles; and
 d. drying the coated particles, for example at about 40° C. for about 24 hours.

A stabilized product of the triggering composition may be obtained by subjecting the coated substrate to oven heating at a temperature above the glass transition temperature (Tg) of the plasticized acrylic polymer for the required time period, the optimum values for temperature and time for the particular formulation being determined experimentally.

The cured, coated compositions of the present invention provide a stable dissolution profile when stored for extended periods of time at room temperature and ambient humidity (e.g., long term (real time) testing), and when tested under accelerated storage conditions.

A superabsorbent polymer as set forth in embodiments of the present invention is obtained by the initial polymerization of from about 55% to about 99.9% by weight of the superabsorbent polymer of polymerizable unsaturated acid group containing monomer. A suitable monomer may include any of those containing carboxyl groups, such as acrylic acid, methacrylic acid, or 2-acrylamido-2-methylpropanesulfonic acid, or mixtures thereof. At least about 50% by weight, or at least about 75% by weight of the acid groups may be carboxyl groups.

The acid groups may be neutralized to the extent of at least about 25 mol %, that is, the acid groups may be present as sodium, potassium, or ammonium salts. In some aspects, the degree of neutralization may be at least 40 mol % or at least about 50 mol %, or at least 60 mol %, or at least 70 mol %, or from about 40 mol % to about 60 mol %. In some aspects, it is desirable to utilize polymers obtained by polymerization of acrylic acid or methacrylic acid, the carboxyl groups of which are neutralized to the extent of from about 50 mol % to about 80 mol %, in the presence of internal crosslinking agents.

In some aspects, the suitable monomer that may be copolymerized with the ethylenically unsaturated monomer may include, but is not limited to acrylamide, methacrylamide, hydroxyethyl acrylate, dimethylaminoalkyl (meth)-acrylate, ethoxylated (meth)-acrylates, dimethylaminopropylacrylamide, or acrylamidopropyltrimethylammonium chloride. Such monomer may be present in a range of from 0% to about 40% by weight of the copolymerized monomer.

The superabsorbent polymer of the invention may also include internal crosslinking agents. The internal crosslinking agent has at least two ethylenically unsaturated double bonds, or one ethylenically unsaturated double bond and one functional group that is reactive toward acid groups of the polymerizable unsaturated acid group containing monomer, or several functional groups that are reactive towards acid groups may be used as the internal crosslinking component and is desirably present during the polymerization of the polymerizable unsaturated acid group containing a monomer.

Examples of internal crosslinking agents include, but are not limited to, aliphatic unsaturated amides, such as methylenebisacryl- or -methacrylamide or ethylenebisacrylamide; aliphatic esters of polyols or alkoxylated polyols with ethylenically unsaturated acids, such as di(meth)acrylates or tri (meth)acrylates of butanediol or ethylene glycol, polyglycols or trimethylolpropane; di- and triacrylate esters of trimethylolpropane which may be oxyalkylated, desirably ethoxylated, with about 1 to about 30 mol of alkylene oxide; acrylate and methacrylate esters of glycerol and pentaerythritol and of glycerol and pentaerythritol oxyethylated with desirably about 1 to about 30 mol of ethylene oxide; allyl compounds, such as allyl(meth)acrylate, alkoxylated allyl(meth)acrylate reacted with desirably about 1 to about 30 mol of ethylene oxide, triallyl cyanurate, triallyl isocyanurate, maleic acid diallyl ester, poly-allyl esters, tetraallyloxyethane, triallylamine, tetraallylethylenediamine, diols, polyols, hydroxy allyl or acrylate compounds and allyl esters of phosphoric acid or phosphorous acid; and monomers that are capable of crosslinking, such as N-methylol compounds of unsaturated amides, such as of methacrylamide or acrylamide, and the ethers derived there from. Ionic crosslinkers such as multivalent metal salts may also be employed. Mixtures of the crosslinking agents mentioned may also be employed. The content of the internal crosslinking agents is from about 0.001% to about 5% by weight such as from about 0.2% to about 3% by weight based on the total amount of the polymerizable unsaturated acid group containing monomer.

In another embodiment of the present invention, from about 0.05 to about 10 wt %, or from about 0.2 wt % to about 5 wt %, from about 0.2 wt % to about 5 wt %, of a blowing agent (based on the total monomer solution weight) may be added to the monomer solution. The blowing agents may be added prior to, simultaneously with, or immediately after polymerization is initiated. The blowing agents are not as effective if added after the hydrogel is formed, nor are they effective when added after chopping or drying the gelled polymer. By varying the amount of the blowing agent, the release of the blowing agent may be timed to provide the most advantageous microcellular structure of the resulting hydrogel.

The blowing agents may include any carbonate or bicarbonate containing salt, or mixed salt, sodium carbonate, potassium carbonate, ammonium carbonate, magnesium carbonate, or magnesium (hydrolytic) carbonates, calcium carbonate, barium carbonate, bicarbonates and hydrates of these, azo compounds or other cations, as well as naturally occurring carbonates, such as dolomite, or mixtures thereof. Blowing agents may include carbonate salts of multivalent cations, such as $Mg^{2+}$, $Ca^{2+}$, $Zn^{2+}$, and the like. Although certain of the multivalent transition metal cations may be used, some of them, such as ferric cation, may cause color staining and may be subject to reduction-oxidation reactions or hydrolysis equilibria in water. This may lead to difficulties in quality control of the final polymeric product. Also, other multivalent cations, such as $Ni^{2+}$, $Ba^{2+}$, $Cd^{2+}$, and $Hg^{2+}$, would be unacceptable because of potential toxic or skin sensitizing effects. A preferred blowing agent is $MgCO_3$, which may also be represented by the formula $(MgCO_3)_4 \cdot Mg(OH)_2 \cdot 5H_2O$. Another preferred blowing agent is $(NH_4)_2CO_3$. The blowing agents $MgCO_3$ and $(NH_4)_2CO_3$ may also be used in mixtures.

Such blowing agents may be resin encapsulated. Encapsulation of such blowing agents provides a controllable delayed release of a gas such as carbon dioxide when dispersed in a monomer solution that is heated or polymerized in accordance with the present invention. The method for encapsulation comprises coating a particular blowing agent with a resin that may be diluted in a solvent solution. The solvent utilized may be an organic or inorganic solvent such as water depending on the nature of the coating to be applied. A second coating, generally called a sealing coating, may be applied on the encapsulated blowing agent.

Resins employed in encapsulating the blowing agent in the superabsorbent polymers of the present invention may include but are not limited to natural and synthetic resins, polyolefins (for example, polyethylene and polypropylene), olefin copolymers (for example, copolymers of ethylene and ethylvinylacetate), polyaromatic olefins, styrenic compounds and polymerized halo-diolefins (for example, neoprene, ethylene-propylene copolymers, polyvinyl chloride, polyvinyl alcohol, polyvinyl acetate, polyacrylic acid derivatives, polycarbonate, polyesters, poly-alpha methylstyrene and polystyrene), starch, gelatin, and cellulose. Preferred resin materials include polyols such as polyethylene glycol.

From 0 to about 95% by weight of the appropriate solvent may be added to the resin to form a solution and coated on to the blowing agent. Resin solution may be applied on the blowing agent in an amount from about 10% to about 80% by weight of the encapsulation compound, or from about 30% to about 70% by weight of the encapsulation compound, and may be applied with any encapsulating method commonly employed in the art including, but not limited to, tumbling or spraying. The purpose of the encapsulating resin is to delay the gas release by the blowing agent in the monomer solution until a later stage of the polymerization process, allowing control of and improving the microcellular structure of the hydrogel.

The encapsulation of the blowing agent by the resinous substrate may be accomplished at room temperature, but elevated temperatures are preferred. The resinous substrate may be from about 30 to about 70% by weight of the encapsulated compound.

The superabsorbent polymer composition of the invention may also include from about 50 to about 1000 ppm of a thermal initiator based on the polymerizable unsaturated acid group containing monomer. Thermal initiators may include persulfates such as sodium persulfate, potassium persulfate, and ammonium persulfate; peroxides such as hydrogen peroxide, benzoyl peroxide, t-butyl peroxide, and methyl ethyl ketone peroxide; peroxyesters such as t-butylperoxypivalate, t-amylperoxypivalate, t-amylperoxy-2-ethylhexanoate and t-butylperoxyisobutyrate; and azo compounds such as azonitrile compounds, azoamidine compounds, cyclic azoamidine compounds, azoamide compounds, alkylazo compounds, 2,2'-azobis(2-amidinopropane) dihydrochloride, and 2,2'-azobis(2-(2-imidazolin-2-yl)propane)dihydrochloride.

In some aspects, initiators may be used for initiation of the free-radical polymerization. Suitable initiators may include, but are not limited to, azo or peroxo compounds, redox systems or UV initiators, sensitizers, and/or radiation.

After polymerization, the superabsorbent polymer becomes a crosslinked hydrogel that may be prepared into superabsorbent polymer particles. The superabsorbent polymer particles may then be surface crosslinked by the addition of a surface crosslinking agent and heat-treatment. In general, surface crosslinking is a process that is believed to increase the crosslink density of the polymer matrix in the vicinity of the superabsorbent particle surface with respect to the crosslinking density of the particle interior.

In some particular aspects, desirable surface crosslinking agents include chemicals with one or more functional groups that are reactive toward pendant groups of the polymer chains, typically the acid groups. The surface crosslinking agent may be present in an amount of from about 0.001% to about 5% by weight of the dry superabsorbent polymer composition, and such as from about 0.1% to about 3% by weight, and such as from about 0.1% to about 1% by weight, based on the weight of the dry superabsorbent polymer composition. Applicants have found that a heat treatment step after addition of the surface crosslinking agent is desirable.

Surface crosslinking agents are chemical compounds that may contain functional groups capable of reacting with carboxylic acid or carboxyl groups. Surface crosslinking agents may include two functional groups such as some alcohol, amine, aldehyde, and carbonate groups may be used. Crosslinker molecules having multiple different functions may also be employed, such as polyols, polyamines, polyaminoalcohols, and alkylene carbonates. Ethylene glycol, diethylene glycol, triethylene glycol, polyethylene glycol, glycerol, polyglycerol, propylene glycol, diethanolamine, triethanolamine, polypropylene glycol, block copolymers of ethylene oxide and propylene oxide, sorbitan fatty acid esters, ethoxylated sorbitan fatty acid esters, trimethylolpropane, ethoxylated trimethylolpropane, pentaerythritol, ethoxylated pentaerythritol, polyvinyl alcohol, sorbitol, ethylene carbonate, and propylene carbonate may be used. Polyols and ethylene carbonate may be used as surface crosslinking agents.

Surface crosslinking agents may be an alkylene carbonate followed by heating to effect surface crosslinking, which may improve the surface crosslinking density and the gel strength characteristics of the superabsorbent polymer particle. More specifically, the surface crosslinking agent may be coated onto the superabsorbent polymer particulate by mixing the polymer particulate with an aqueous alcoholic solution of the alkylene carbonate surface crosslinking agent. The amount of alcohol may be determined by the solubility of the alkylene carbonate and is kept as low as possible for various reasons. Suitable alcohols are methanol, isopropanol, ethanol, butanol, or butyl glycol, as well as mixtures of these alcohols. In some aspects, the solvent desirably is water, which typically is used in an amount of about 0.3% by weight to about 5.0% by weight, based on the weight of the dry superabsorbent polymer. In other aspects, the alkylene carbonate surface crosslinking agent may be dissolved in water without any alcohol. In still other aspects, the alkylene carbonate surface crosslinking agent may be applied from a powder mixture, for example, with an inorganic carrier material, such as silicone dioxide ($SiO_2$), or in a vapor state by sublimation of the alkylene carbonate.

To achieve the desired surface crosslinking properties, the alkylene carbonate is distributed evenly on the particulate superabsorbent polymer. For this purpose, mixing is effected in suitable mixers known in the art, such as fluidized bed mixers, paddle mixers, rotary drum mixers, or twin-worm mixers. It is also possible to carry out the coating of the particulate superabsorbent polymer during one of the process steps in the production of the particulate superabsorbent polymer. In one particular aspect, a suitable process for this purpose is the inverse suspension polymerization process.

The heat treatment, which may follow the coating treatment, may be carried out as follows. In general, the heat treatment is at a temperature of from about 100° C. to about 300° C. Lower temperatures are possible if highly reactive epoxide crosslinking agents are used. However, if alkylene carbonates are used, then the thermal treatment is suitably at a temperature of from about 150° C. to about 250° C. In this particular aspect, the treatment temperature depends on the swell time and the kind of alkylene carbonate. For example, at a temperature of about 150° C., the thermal treatment may be carried out for one hour or longer. In contrast, at a temperature of about 250° C., a few minutes (e.g., from about 0.5 minutes to about 5 minutes) are sufficient to achieve the desired surface cross-linking properties. The thermal treatment may be carried out in conventional dryers or ovens known in the art.

The superabsorbent polymer composition of the present invention may further include from 0 to about 5 wt % of a multivalent metal salt on the surface of the polymer, based on the weight of the dry superabsorbent polymer composition. The multivalent metal salt is preferably water soluble. Examples of metal cations include the cations of Al, Fe, Zr, Mg, and Zn. The metal cation may have a valence of at least +3, such as with Al. Examples of anions in the multivalent metal salt include halides, chlorohydrates, sulfates, lactate, nitrates, and acetates. Examples of such multivalent metal salts include aluminum sulfate, and aluminum lactate. A form of aluminum sulfate is hydrated aluminum sulfate, preferably aluminum sulfate having from 12 to 14 waters of hydration. Mixtures of multivalent metal salts may be employed.

The polymer and multivalent metal salt suitably may be mixed by dry blending, or in solution such as an aqueous solution, using means well known to those skilled in the art. With dry blending, a binder may be employed in an amount which is sufficient to ensure that a substantially uniform mixture of the salt and the superabsorbent polymer is maintained. The binder may be water or a nonvolatile organic compound having a boiling point of at least 150° C. Examples of binders include water, polyols such as propylene glycol, glycerin, and poly(ethylene glycol).

In some aspects, the superabsorbent polymer composition of the present invention may include up to about 5% by weight, and from about 0.001% to about 5% by weight, and from about 0.01% to about 0.5% by weight of the dry superabsorbent polymer composition of a polymeric coating, such as a thermoplastic coating, or a cationic coating, or a combination of a thermoplastic coating and a cationic coating. In some particular aspects, the polymeric coating may be a polymer that may be a solid, emulsion, suspension, colloidal, or solubilized state, or combinations thereof. Polymeric coatings suitable for this invention may include, but are not limited to, a thermoplastic coating having a thermoplastic melt temperature, wherein the polymeric coating may be applied to the particle surface coincident with, or followed by a temperature of the treated superabsorbent polymer particle at about the thermoplastic melt temperature.

Examples of thermoplastic polymers that may also be employed include, but are not limited to, polyolefin, polyethylene, polyester, polyamide, polyurethane, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins, such as blends of PP, EVA, EMA, EEA, EBA, HDPE, MDPE, LDPE, LLDPE, and/or VLDPE. A thermoplastic polymer may be functionalized to have additional benefits such as water solubility or dispersability.

Polymeric coatings of this invention may also include a cationic polymer. A cationic polymer as used herein refers to a polymer or mixture of polymers comprising a functional group, or groups, having a potential of becoming positively charged ions upon ionization in an aqueous solution. Suitable functional groups for a cationic polymer include, but are not limited to, primary, secondary, or tertiary amino groups, imino groups, imido groups, amido groups, and quaternary ammonium groups. Examples of synthetic cationic polymers include, but are not limited to, the salts or partial salts of poly(vinyl amines), poly(allylamines), poly(ethylene imine), poly(amino propanol vinyl ethers), poly(acrylamidopropyl trimethyl ammonium chloride), and poly(diallyldimethyl ammonium chloride). Poly(vinyl amines) include, but are not limited to, LUPAMIN®9095 available from BASF Corporation, Mount Olive, N.J. Examples of natural-based cationic polymers include, but are not limited to, partially deacetylated chitin, chitosan, and chitosan salts. Synthetic polypeptides such as polyasparagins, polylysines, polyglutamines, and polyarginines are also suitable cationic polymers.

The superabsorbent polymer compositions according to the invention may include from 0 to about 5 wt %, or from 0.05 to about 2.0 wt %, of a multivalent metal salt, based on the dry superabsorbent polymer composition. The multivalent metal salt may be applied to the surface of the superabsorbent polymer composition. The multivalent metal salt may be water soluble. Examples of metal cations include the cations of Al, Fe, Zr, Mg, and Zn. The metal cation may have a valence of at least +3, with $Al^{3+}$ being most preferred. Examples of anions in the multivalent metal salt include halides, chlorohydrates, sulfates, lactates, nitrates and acetates, with chlorides, sulfates, chlorohydrates, and acetates being preferred, chlorohydrates and sulfates being more preferred, and sulfates being the most preferred. Aluminum sulfate is the most preferred multivalent metal salt and is readily commercially available. The multivalent metal salt may be an aluminum sulfate such as hydrated aluminum sulfate, such as aluminum sulfate having from 12 to 14 waters of hydration. The multivalent metal salt may be aluminum lactate. Mixtures of multivalent metal salts may be employed.

The superabsorbent polymer compositions according to the invention may include from about 0.01% to about 2% by weight or from about 0.01% to about 1% by weight based on the dry superabsorbent polymer composition of a water-insoluble inorganic metal compound. The water-insoluble inorganic metal compound may be applied to the surface of the superabsorbent polymer composition. The water-insoluble inorganic metal compounds may include, but are not limited to, a cation selected from aluminum, titanium, calcium, or iron and an anion selected from phosphate, borate, or chromate. Examples of water-insoluble inorganic metal compounds include aluminum phosphate and an insoluble metal borate. The insoluble metal borate may be selected from titanium borate, aluminum borate, iron borate, magnesium borate, manganese borate, or calcium borate. The chemical formula TiBO will be used herein to designate titanium borate and analogous compounds such as titanium (III) borate $TiBO_3$. In addition, the chemical formulation also designates the case when titanium (III) borate $TiBO_3$ is treated with hydrogen peroxide to obtain titanium (IV) borate. The inorganic metal compound may have a mass median particle size of less than about 2 µm, and may have a mass median particle size of less than about 1 µm.

The inorganic metal compound may be applied in the dry physical form to the surface of the superabsorbent polymer particles. For this, the superabsorbent polymer particles may be intimately mixed with the finely divided inorganic metal compound. The finely divided inorganic metal compound may be added at about room temperature to the superabsorbent polymer composition particles and mixed in until an about homogeneous mixture is present. For this purpose, mixing is effected in suitable mixers known in the art, such as fluidized bed mixers, paddle mixers, rotary drum mixers, or twin-worm mixers. The mixing of the superabsorbent polymer particles with the finely divided water-insoluble inorganic metal compound may take place before or after any surface crosslinking, for example during the application of the surface crosslinking agent.

Alternatively, a suspension of a finely divided water-insoluble inorganic metal compounds may be prepared and applied to a particulate water absorbent polymer. The suspension may be applied, for example, by spraying. Useful dispersion media for preparing the suspension include water, organic solvents such as alcohols, for example methanol, ethanol, isopropanol, ketones, for example acetone, methyl ethyl ketone, or mixtures of water with the aforementioned organic solvents. Other useful dispersion media include dispersion aids, surfactants, protective colloidals, viscosity modifiers, and other auxiliaries to assist in the preparation of the suspension. The suspension may be applied in conventional reaction mixers, or mixing and drying systems as described above at a temperature in the range from room temperature to less than the boiling point of the dispersion medium, or at about room temperature. It is appropriate to combine the application of the suspension with a surface crosslinking step by dispersing the finely divided water-insoluble metal salt in the solution of the surface crosslinking agent. Alternatively, the suspension may also be applied before or after the surface crosslinking step. The application of the slurry may be followed by a drying step.

In some aspects, the superabsorbent polymer compositions according to the invention may also include from 0% to about 5%, or in the alternative from about 0.01% to about 3%, by weight of the dry superabsorbent polymer composition of silica. Examples of silica include fumed silica, precipitated silica, silicon dioxide, silicic acid, and silicates. In some particular aspects, microscopic noncrystalline silicon dioxide may be desirable. Products include SIPERNAT®22S and AEROSIL®200 available from Degussa Corporation, Parsippany, N.J. In some aspects, the particle diameter of the inorganic powder may be 1,000 µm or smaller, such as 100 µm or smaller.

In some aspects, the superabsorbent polymer compositions may also include from 0% to about 30% by weight of the dry superabsorbent polymer composition, such as from about 0.1% to about 5% by weight, of water-soluble polymers based by weight of the dry superabsorbent polymer composition, of partly or completely hydrolyzed polyvinyl acetate, polyvinylpyrrolidone, starch or starch derivatives, polyglycols, polyethylene oxides, polypropylene oxides, or polyacrylic acids.

In some aspects, additional surface additives may optionally be employed with the superabsorbent polymer particles, such as odor-binding substances, such as cyclodextrins, zeolites, inorganic or organic salts, and similar materials, anti-caking additives, flow modification agents, surfactants, viscosity modifiers, and the like. In addition, surface additives may be employed that perform several roles during surface modifications. For example, a single additive may be a surfactant, viscosity modifier, and may react to crosslink polymer chains.

In some aspects, the superabsorbent polymer compositions of the present invention may, after a heat treatment step, be treated with water so that the superabsorbent polymer composition has water content of up to about 10% by weight of the superabsorbent polymer composition. This water may be added with one or more of the surface additives from above added to the superabsorbent polymer.

The superabsorbent polymer compositions according to the invention are desirably prepared by two methods. The composition may be prepared continuously or discontinuously in a large-scale industrial manner, the after-crosslinking according to the invention being carried out accordingly.

According to one method, the partially neutralized monomer, such as acrylic acid, may be converted into a gel by free-radical polymerization in aqueous solution in the presence of crosslinking agents and any further components, and the gel may be comminuted, dried, ground, and sieved off to the desired particle size. For the present invention, the size of the high-capacity superabsorbent polymer composition particles is dependent on manufacturing processes including milling and sieving. It is well known to those skilled in the art that particle size distribution of the superabsorbent polymer particles resembles a normal distribution or a bell shaped curve. It is also known that for various reasons, the normal distribution of the particle size distribution may be skewed in either direction.

The superabsorbent polymer particles of the present invention generally include particle sizes ranging from about 50 to about 1000 μm, or from about 150 to about 850 μm. The present invention may include at least about 40 wt % of the particles having a particle size from about 300 μm to about 600 μm, at least about 50 wt % of the particles having a particle size from about 300 μm to about 600 μm, or at least about 60 wt % of the particles having a particle size from about 300 μm to about 600 μm as measured by screening through a U.S. standard 30 mesh screen and retained on a U.S. standard 50 mesh screen. In addition, the size distribution of the superabsorbent polymer particles of the present invention may include less than about 30% by weight of particles having a size greater than about 600 microns, and less than about 30% by weight of particles having a size of less than about 300 microns as measured using for example a RO-TAP® Mechanical Sieve Shaker Model B available from W. S. Tyler, Inc., Mentor, Ohio.

While the form of particles may be used by way of example of the physical form of superabsorbent polymer composition, the invention is not limited to this form and is applicable to other forms such as fibers, foams, films, beads, rods, and the like, as discussed above. In some aspects, when the superabsorbent polymer composition exists as particles or in granule form, it is desirable that these particles have a size of from about 150 μm to about 850 μm based on the sieving process that is well known in the superabsorbent industry.

According to another method, inverse suspension and emulsion polymerization may also be used for preparation of the products according to the invention. According to these processes, an aqueous, partly neutralized solution of monomer, such as acrylic acid, may be dispersed in a hydrophobic, organic solvent with the aid of protective colloids and/or emulsifiers, and the polymerization is started by free radical initiators. The internal crosslinking agents may be either dissolved in the monomer solution and are metered in together with this, or are added separately and optionally during the polymerization. The addition of a water-soluble polymer as the graft base optionally takes place via the monomer solution or by direct introduction into the organic solvent. The water is then removed azeotropically from the mixture, and the polymer is filtered off and optionally dried. Internal crosslinking may be carried out by polymerizing-in a polyfunctional crosslinking agent dissolved in the monomer solution and/or by reaction of suitable crosslinking agents with functional groups of the polymer during the polymerization steps.

The superabsorbent polymer compositions of the present invention may have a vortex time as measured by the test procedure set forth herein, of about 45 seconds or less, or a vortex time of from about 45 seconds to about 5 seconds, or from about 40 seconds to about 10 seconds, or from about 35 seconds to about 15 seconds. In addition the superabsorbent polymer compositions may have a Centrifuge Retention Capacity (CRC) as measured by the CRC Test of from about 15 g/g to about 60 g/g, or about 20 g/g or more, or from about 20 g/g to about 60 g/g, or about 25 g/g or more, or from about 25 g/g to about 60 g/g.

The result of these methods is a superabsorbent preproduct. A superabsorbent preproduct as used herein is produced by repeating all of the steps for making the superabsorbent, up to and including drying the material, and coarse grinding in a crusher, and removing particles greater than about 850 μm and smaller than about 150 μm.

Test Procedures

Unless otherwise stated, the test fluid used in all the test methods described below is an aqueous 0.9 wt % sodium chloride solution, such as that available from Ricca Chemical Company (Arlington, Tex.). Unless otherwise stated, all tests were conducted at about 70° F. and between 10 and 60% relative humidity.

Centrifuge Retention Capacity Test

The Centrifuge Retention Capacity (CRC) Test measures the ability of the superabsorbent polymer to retain liquid therein after being saturated and subjected to centrifugation under controlled conditions. The resultant retention capacity is stated as grams of liquid retained per gram weight of the sample (g/g). The sample to be tested is prepared from particles that are pre-screened through a U.S. standard 30-mesh screen and retained on a U.S. standard 50-mesh screen. As a result, the superabsorbent polymer sample comprises particles sized in the range of about 300 to about 600 microns. The particles may be pre-screened by hand or automatically.

The retention capacity is measured by placing about 0.2 grams of the pre-screened superabsorbent polymer sample into a water-permeable bag that will contain the sample while allowing a test solution (0.9 weight percent sodium chloride in distilled water) to be freely absorbed by the sample. A heat-sealable tea bag material, such as that available from Dexter Corporation (having a place of business in Windsor Locks, Conn., U.S.A.) as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals are about 0.25 inches inside the edge of the material. After the sample is placed in the pouch, the remaining open edge of the pouch is also heat-sealed. Empty bags are also made to serve as controls. Three samples are prepared for each superabsorbent polymer composition to be tested.

The sealed bags are submerged in a pan containing the test solution at about 23° C., making sure that the bags are held down until they are completely wetted. After wetting, the samples remain in the solution for about 30 minutes, at which time they are removed from the solution and temporarily laid on a non-absorbent flat surface.

The wet bags are then placed into the basket, wherein the wet bags are separated from each other and are placed at the outer circumferential edge of the basket, wherein the basket is of a suitable centrifuge capable of subjecting the samples to a g-force of about 350. One suitable centrifuge is a CLAY ADAMS DYNAC II, model #0103, having a water collection basket, a digital rpm gauge, and a machined drainage basket adapted to hold and drain the flat bag samples. Where multiple samples are centrifuged, the samples are placed in opposing positions within the centrifuge to balance the basket when spinning. The bags (including the wet, empty bags) are centrifuged at about 1,600 rpm (e.g., to achieve a target g-force of about 290 g force with a variance from about 280 to about 300 g force), for 3 minutes. G force is defined as a unit of inertial force on a body that is subjected to rapid acceleration or gravity, equal to 9.8 m/sec$^2$ at sea level. The bags are removed and weighed, with the empty bags (controls) being weighed first, followed by the bags containing the superabsorbent polymer composition or absorbent composition samples. The amount of solution retained by the superabsorbent polymer sample, taking into account the solution retained by the bag itself, is the centrifuge retention capacity (CRC) of the superabsorbent polymer, expressed as grams of fluid per gram of superabsorbent polymer. More particularly, the retention capacity is determined by the following equation:

$$\frac{\text{sample/bag after centrifuge} - \text{empty bag after centrifuge} - \text{dry sample weight}}{\text{dry sample weight}}$$

The three samples are tested, and the results are averaged to determine the Centrifuge Retention Capacity (CRC) of the superabsorbent polymer composition. Deviation of measurements of CRC may be +/−0.5 and it is known that CRC may vary from batch to batch of superabsorbent polymer composition.

Superabsorbent Polymer pH Test

This test measures the pH of a solution of superabsorbent polymer in 0.9% saline.

Materials Needed:
1. pH meter.
2. pH electrode (Brinkman, Unitrode, PN#20910674 or equivalent)
3. 250 ml beaker.
4. Stir Plate capable of 500 rpm.
5. Stir Bar (approximately 3 cm).
6. 0.9% Saline w/w (Aqueous Sodium Chloride Solution, part number 7213.09-5 from Ricca, or equivalent).)
7. Weigh boat.
8. Balance (accurate to 0.0001 grams).
9. Timer (NIST traceable).
10. Graduated Cylinder (class A, 100 ml capacity)
11. UltraPure water Procedure:
1. Obtain a 250 ml beaker.
2. Measure 150 ml of 0.9% saline into graduated cylinder, pour saline into 250 ml beaker.
3. Place a stir bar into beaker.
4. Place weigh boat onto balance and tare.
5. Weigh 1.0 g±0.001 superabsorbent into weigh boat.
6. Pour sample into 250 ml beaker
7. Label beaker with sample I.D.
8. Place beaker on stir plate at 500 rpm.
9. Start timer—3 min. Allow sample to stir for 3 min.
10. When 3 min has expired immerse pH electrode into beaker.
11. Continue to gently stir sample.
12. Set timer for 6 min.
13. Start timer and measure pH.
14. When time has expired (6 min) record measured value.
15. Remove pH electrode from sample and rinse thoroughly with ultrapure water.

Vortex Time

General Description: The vortex test measures the amount of time in seconds required for 2 grams of a superabsorbent polymer composition to close a vortex created by stirring 50 milliliters of saline solution at 600 revolutions per minute on a magnetic stir plate. The time it takes for the vortex to close is an indication of the free swell absorbing rate of the superabsorbent polymer composition.

Equipment & Materials
1. Beaker, 100 milliliter
2. Programmable magnetic stir plate, capable of providing 600 revolutions per minute (such as that commercially available from PMC Industries as Dataplate.®. Model #721).
3. Magnetic stir bar without rings, 7.9 millimeters.times.32 millimeters, Teflon.™. covered (such as that commercially available from Baxter Diagnostics, under the trade designation S/PRIM. brand single pack round stirring bars with removable pivot ring).
4. Stopwatch
5. Balance, accurate to +/−0.01 gram
6. Saline solution, 0.87 w/w percent, Blood Bank Saline available from Baxter Diagnostics (considered, herein to be the equivalent of 0.9 weight percent saline)
7. Weighing paper
8. Room with standard condition atmosphere: Temperature=23° C.+/−1° C. and Relative Humidity=50%+/−0.2%.

Test Procedure
1. Measure 50 g+/− 0.01 gram of saline solution into the 100 milliliter beaker.
2. Place the magnetic stir bar into the beaker.
3. Program the magnetic stir plate to 600 revolutions per minute.
4. Place the beaker on the center of the magnetic stir plate such that the magnetic stir bar is activated. The bottom of the vortex should be near the top of the stir bar.
5. Weigh out 2 g+/−0.01 gram of the superabsorbent polymer composition to be tested on weighing paper.

NOTE: The superabsorbent polymer composition is tested as received (i.e. as it would go into an absorbent composite such as those described herein). No screening to a specific particle size is done, though the particle size is known to have an effect on this test.

6. While the saline solution is being stirred, quickly pour the superabsorbent polymer composition to be tested into the saline solution and start the stopwatch. The superabsorbent polymer composition to be tested should be added to the saline solution between the center of the vortex and the side of the beaker.
7. Stop the stopwatch when the surface of the saline solution becomes flat and record the time.
8. The time, recorded in seconds, is reported as the Vortex Time.

Swell/Deswell/Reswell Test of the Absorbent Composition

The Swell/Deswell/Reswell test is intended to measure the liquid absorption capacity of the absorbent composition versus time. The layout of the apparatus is shown in FIG. 13.

A suitable apparatus for this test is shown in FIG. 13. At one end of this apparatus is a fluid reservoir 1 containing 0.9% saline solution. The other end of the apparatus is a cylinder 8 for holding absorbent compositions, and a small plastic box 4 for delivering saline solution to absorbent compositions. For example, a Plexiglas cylinder (cylinder inner diameter=25 mm; height=33 mm) with screen filter cloth on bottom (400 mesh=36 microns) can be used for the test. The top plate of box 4 has holes (ca. 1 mm diameter) on it. A piece of filter paper 7 is placed between cylinder 8 and box 4 to ensure good contact of absorbent compositions with saline solution. Box 4 is placed on a stand 5 on an electronic balance 6 which is connected to a computer for recording the weight change of absorbent compositions during the measurement. Box 4 is connected to reservoir 1 through a flexible tubing 3.

Prior to measurement, the height of reservoir 1 is adjusted to proper level so that the liquid surface in reservoir 1 is at the same level as the top surface of box 4.

The test is started by:
1. adding test sample into cylinder 8 and placing a plastic piston on the top of the test sample;
2. placing the cylinder on box 4 such that the bottom of the cylinder is in contact with the liquid; and 3. immediately starting recording the weight change of the test sample.

The test is stopped after 240 minutes. The absorption capacity of the absorbent composition is calculated dividing the liquid uptake by the weight of the superabsorbent polymer in the absorbent composition. The swell/deswell/reswell curve is generated by plotting the absorption capacity versus time.

Release Profile Measurement—Release of Coated Sulfamic Acid

The release of sulfamic acid was determined by soaking the coated sulfamic acid in deionized water at room temperature (23° C.) and measuring the pH of the solution using an ORION pH meter (Model No. 290A) and a pH electrode (Model No. ORION 8-172BNWP).

The coated sulfamic acid (2.00 g) was sealed in a teabag. 1800 g of deionized water was added into a glass beaker with a magnetic stirring bar (10 mm×70 mm). The beaker was placed on a magnetic stirrer, and the solution was stirred at 200 rpm. The teabag was soaked in the water. A small amount of liquid (about 20 g) was taken out at the times specified in Table 1. The actual weight of solution removed was recorded. The pH of the removed solution was measured with the pH meter. The data from the electrode was converted to concentration of released sulfamic acid by using the calibration curve generated with standard solutions of sulfamic acid. The percentage of the released sulfamic acid can be calculated based on the weight of released sulfamic acid and the total weight of sulfamic acid in the coated sample.

Release of Coated Calcium Formate

The release of calcium formate was determined according to the same procedure as for the "Release profile measurement—Release of coated sulfamic acid" except that the concentration of release calcium formate was measured using a Varian Inductively Coupled Plasma (Model No. Vista MPX Radical).

Release of Coated Sodium Carbonate

The release of sodium carbonate was measured according to the same procedure as for the "Release profile measurement—Release of coated sulfamic acid" except that the released sodium carbonate was determined by following the release of sodium ion using an Accumet sodium selective electrode (Available from Fisher Scientific, #13-620-503).

EXAMPLES

The present invention may be better understood with reference to the figures and the following examples. The following examples and preproducts for the examples are provided to illustrate the invention and do not limit the scope of the claims. Unless otherwise stated, all parts and percentages are by weight.

Superabsorbent Polymer Compositions

Preproduct B

Into a polyethylene container equipped with an agitator and cooling coils was added 1167 grams of 50% NaOH and 2032 grams of distilled water and cooled to 20° C. 500 grams of glacial acrylic acid was then added to the caustic solution and the solution again cooled to 20° C. 3.75 grams of polyethylene glycol monoallylether acrylate, 3.75 grams of ethoxylated trimethylol propane triacrylate SARTOMER®454 product, and 1000 grams of glacial acrylic acid were added to the first solution, followed by cooling to 4-6° C. Nitrogen was bubbled through the monomer solution for about 10 minutes. The cooling coils were removed from the container. Immediately prior to the addition of initiators, 47 g of the coated FMC grade 50 sodium carbonate was added to the monomer solution as a blowing agent (The coated blowing agent was prepared by spraying 9 grams of polyethylene glycol 8000 solution (16.5 wt % in water) onto 300 grams of sodium carbonate powder. The coated powder was relaxed at room temperature for at least 1 hour before it was used in the polymerization batch). To the monomer solution was added 50 g of 1% by weight of $H_2O_2$ aqueous solution, 150 g of 2 wt % aqueous sodium persulfate solution, and 45 g of 0.5 wt % aqueous sodium erythorbate solution to initiate polymerization reaction. The agitator was stopped and the initiated monomer was allowed to polymerize for 20 minutes. The resulting hydrogel was chopped and extruded with a Hobart 4M6 commercial extruder, followed by drying in a Procter & Schwartz Model 062 forced air oven at 175° C. for 10 minutes with up flow and 6 minutes with down flow air on a 20 in×40 in perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 850 μm and smaller than 150 μm. The product had a CRC of 38 g/g and a vortex time of 32 seconds.

Preproduct C

Into a polyethylene container equipped with an agitator and cooling coils was added 1333 grams of 50% NaOH and 3988 grams of distilled water and cooled to 20° C. 800 grams of glacial acrylic acid was then added to the caustic solution and the solution again cooled to 20° C. 3.6 grams of polyethylene glycol monoallylether acrylate, 3.6 grams of ethoxylated trimethylol propane triacrylate SARTOMER®454 product, and 1600 grams of glacial acrylic acid were added to the first solution, followed by cooling to 4-6° C. Nitrogen was bubbled through the monomer solution for about 10 minutes. The cooling coils were removed from the container. To the monomer solution was added 80 g of 1% by weight of $H_2O_2$ aqueous solution, 120 g of 2 wt % aqueous sodium persulfate solution, and 72 g of 0.5 wt % aqueous sodium erythorbate solution to initiate polymerization reaction. The agitator was stopped and the initiated monomer was allowed to polymerize for 20 minutes. The resulting hydrogel was chopped and extruded with a Hobart 4M6 commercial extruder, followed by drying in a Procter & Schwartz Model 062 forced air oven at 175° C. for 10 minutes with up flow and 6 minutes with down flow air on a 20 in×40 in perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 850 μm and smaller than 150 μm. The product had a CRC of 36.2 g/g and a vortex time of 60 seconds.

Preproduct D

Into a polyethylene container equipped with an agitator and cooling coils was added 972 grams of 50% NaOH and 1,976 grams of distilled water and cooled to 20° C. 583 grams of glacial acrylic acid was then added to the caustic solution and the solution again cooled to 20° C. 2.625 grams of polyethylene glycol monoallylether acrylate, 2.625 grams of ethoxylated trimethylol propane triacrylate SARTOMER®454 product, and 1,167 grams of glacial acrylic acid were added to the first solution, followed by cooling to 4-6° C. Nitrogen was bubbled through the monomer solution for about 10 minutes. The cooling coils were removed from the container. Immediately prior to the addition of initiators, 51.8 g of the coated FMC grade 50 sodium carbonate was added to the monomer solution as a blowing agent (The coated blowing agent was prepared by spraying 9 grams of polyethylene glycol 8000 solution (16.5 wt % in water) onto 300 grams of sodium carbonate powder. The coated powder was relaxed at room temperature for at least 1 hour before it was used in the polymerization batch). To the monomer solution was added 50 g of 1% by weight of $H_2O_2$ aqueous solution, 150 g of 2 wt % aqueous sodium persulfate solution, and 45 g of 0.5 wt % aqueous sodium erythorbate solution to initiate polymerization reaction. The agitator was stopped and the initiated monomer was allowed to polymerize for 20 minutes. The resulting hydrogel was chopped and extruded with a Hobart 4M6 commercial extruder, followed by drying in a Procter & Schwartz Model 062 forced air oven at 175° C. for 10 minutes with up flow and 6 minutes with down flow air on a 20 in×40 in perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 850 μm and smaller than 150 μm. The product had a CRC of 34.1 g/g and a vortex time of 29 seconds.

Preproduct E

Preproduct E is produced using the method of making Preproduct C except that the amount of 50% NaOH, polyethylene glycol monoallylether acrylate, and ethoxylated trimethylol propane triacrylate was changed to 1066 grams, 2.4 grams, and 2.4 grams, respectively. The product had a CRC of 34.1 g/g and vortex time of 70 seconds.

Preproduct F

Preproduct F was produced following the same method as Preproduct D, except that the amount of polyethylene glycol monoallylether acrylate, and ethoxylated trimethylol propane triacrylate was changed 1.75 grams, and 1.75 grams, respectively. The product had a CRC of 40.1 g/g and vortex time of 26.3 seconds.

Superabsorbent Polymer Composition A (SAP-A)

Superabsorbent polymer composition A is a commercially available superabsorbent product FAVOR®SXM-9300, manufactured by Stockhausen Inc., Greensboro, N.C. It has a degree of neutralization from about 65% to about 75%.

Superabsorbent Polymer Composition B (SAP-B)

Preproduct B was coated with 0.5% of Sipernat®22s, 1 wt % ethylene carbonate, and 3 wt % water using a 25 wt % aqueous solution. The coated Preproduct B was then heated in a convection oven at 185° C. for 45 minutes. The surface crosslinked particulate material was then post treated with 1000 ppm polyethylene glycol 8000 (polyethylene glycol with average molecular weight of 8000) and 5% water.

Superabsorbent Polymer Composition C (SAP-C)

Preproduct C was coated with 0.5% of Sipernat®22s, 1 wt % ethylene carbonate and 3 wt % water using a 25 wt % aqueous solution. The coated Preproduct C was then heated in a convection oven at 150° C. for 40 minutes. The surface crosslinked particulate material was then post treated with 500 ppm polyethylene glycol 8000 (polyethylene glycol with average molecular weight of 8000) and 2% water.

Superabsorbent Polymer Composition D (SAP-D)

Preproduct D was coated with 0.5% of Sipernat®22s, 1 wt % ethylene carbonate and 3 wt % water using a 25 wt % aqueous solution. The coated Preproduct D was then heated in a convection oven at 165° C. for 40 minutes. The surface crosslinked particulate material was then post treated with 500 ppm polyethylene glycol 8000 (polyethylene glycol with average molecular weight of 8000) and 2% water.

Superabsorbent Polymer Composition E (SAP-E)

Preproduct E was coated with 0.5% of Sipernat®22s, 1 wt % ethylene carbonate and 3 wt % water using a 25 wt % aqueous solution. The coated Preproduct E was then heated in a convection oven at 150° C. for 40 minutes. The surface crosslinked particulate material was then post treated with 500 ppm polyethylene glycol 8000 (polyethylene glycol with average molecular weight of 8000) and 2% water.

Superabsorbent Polymer Composition F (SAP-F)

Preproduct F was coated with 0.5% of Sipernat®22s, 1 wt % ethylene carbonate and 3 wt % water using a 20 wt % aqueous solution. The coated Preproduct F was then heated in a convection oven at 155° C. for 40 minutes. The surface crosslinked particulate material was then post treated with 1000 ppm polyethylene glycol 8000 (polyethylene glycol with average molecular weight of 8000) and 5% water.

The foregoing superabsorbent polymer compositions have the properties as shown in the following Table A.

TABLE A

Properties of Superabsorbent Polymer Compositions

| SAP | Centrifuge Retention Capacity (g/g) | Vortex Time (min) | Degree or neutralization (%) | pH |
|---|---|---|---|---|
| SXM9300 | 29.5 | 86 | | |
| SAP-B | 29.4 | 25 | 70 | 6.0 |
| SAP-C | 30 | 67 | 50 | 5.2 |
| SAP-D | 29.4 | 31 | 50 | 5.3 |
| SAP-E | 29.1 | 65 | 40 | 4.9 |
| SAP-F | 33 | 41 | 50 | 5.3 |

Examples of Triggering Compositions

TABLE B

Triggering Compositions

| Triggering Composition | Water-soluble chemical | Coating Polymer | Release profile |
|---|---|---|---|
| $1^{st}$ TC-A | sulfamic acid | 5% EUDRAGIT ® RS 30D | sigmoidal |
| $1^{st}$ TC-B | sulfamic acid | 10% EUDRAGIT ® RS 30D | sigmoidal |
| $1^{st}$ TC-C | Calcium Formate | 5% EUDRAGIT ® RS 30D | singular |
| $1^{st}$ TC-D | Calcium Formate | 10% EUDRAGIT ® RS 30D | singular |
| $1^{st}$ TC-E | Calcium Formate | 2.25% Cellulose Acetate | singular |
| $1^{st}$ TC-F | Calcium Formate | 3% Cellulose Acetate and 3.5% ethyl cellulose | singular |
| $1^{st}$ TC-G | Calcium Formate | 0.1% sodium carboxymethylcellulose | |
| $2^{nd}$ TC-A | Sodium Carbonate | 5% EUDRAGIT ® RS 30D | sigmoidal |
| $2^{nd}$ TC-B | Sodium Carbonate | 10% EUDRAGIT ® RS 30D | sigmoidal |
| $2^{nd}$ TC-C | Sodium Carbonate | 18% EUDRAGIT ® RS 30D | sigmoidal |
| $2^{nd}$ TC-D | Sodium Carbonate | 27% EUDRAGIT ® RS 30D | sigmoidal |
| $2^{nd}$ TC-E | Sodium Carbonate | 2% Maleated propylene | singular |
| $2^{nd}$ TC-F | Sodium Carbonate | 6% Maleated propylene | singular |

The abbreviations SAP-A, SAP-B, SAP-C, SAP-D, SAP-E, SAP-F, $1^{st}$ TC—A, $1^{st}$ TC—B, $1^{st}$ TC—C, $1^{st}$ TC—D, $1^{st}$ TC—E, $1^{st}$ TC—F, $1^{st}$ TC—G, $2^{nd}$ TC—A, $2^{nd}$ TC—B, $2^{nd}$ TC—C, TC—D, $2^{nd}$ TC—E, and $2^{nd}$ TC—F from Tables A and B may be used in the following examples.

Example 1

Preparation of poly(meth)acrylate Coated Sulfamic Acid ($1^{st}$ TC-A and $1^{st}$ TC-B)

A polymer solution or dispersion was sprayed on the surface of water-soluble solid chemicals to form a coating layer. Well suited for this purpose are aqueous poly(meth)acrylate dispersions, for example, EUDRAGIT®RS 30D, commercially available from Evonik Pharma Polymers.

The coating polymer dispersion was prepared according to the following formulation:

| | |
|---|---|
| EUDRAGIT ® RS 30D (30% aqueous dispersion) | 1200 g |
| Triethyl citrate | 36 g |
| Talc | 180 g |
| Water | 1464 g |

The mixture of coating materials was stirred in a container using an overhead stirrer. The mixture was stirred for at least 15 minutes to ensure good mixing before it was used to coat the water-soluble solid chemical.

About 800 g of sulfamic acid particles (particle size between 100-20 mesh, U.S. Sieve Series) obtained from Sigma-Aldrich Company were placed in a Glatt WSG 5 fluidized bed apparatus. The Glatt unit was set up to provide top spray by insertion of a top spray insert and a 150 micron filter bag was utilized. The air used to fluidize the sulfamic acid particles was conditioned to remove water vapor in the air. The coating material was applied at a coating material temperature of about 25° C., an atomizing air pressure of 2.0 bar, and a spray flow rate of 8 g/min/Kg. After the coating material was applied, the coated particles were dried at 40° C. for 24 hours. The coated product was produced having 5% or 10% by weight polymer coating.

The release of sulfamic acid was measured using a pH meter, as described in the Test method for the "Release profile measurement—Release of coated sulfamic acid" above. The results are tabulated in Table 1.

TABLE 1

| Time (min) | $1^{st}$ TC-A (5% coating) | $1^{st}$ TC-B (10% coating) |
|---|---|---|
| 0 | 0.0 | 0.0 |
| 2 | 2.1 | 1.0 |
| 4 | 9.0 | 1.7 |
| 6 | 18.2 | 2.7 |
| 8 | 28.1 | 3.9 |
| 10 | 37.6 | 5.2 |
| 15 | 60.0 | 7.9 |
| 20 | 77.5 | 11.9 |
| 25 | 89.1 | 15.4 |
| 30 | 96.3 | 20.8 |
| 40 | 97.3 | 33.3 |
| 50 | 97.9 | 46.6 |
| 60 | 99.4 | 59.1 |
| 80 | | 78.2 |
| 100 | | 90.4 |

FIG. 1 is a graphical plot of release profiles of poly(meth)acrylate coated sulfamic acid. These triggering compositions showed sigmoidal release profiles. And the release rate was controlled by the amount of coating polymer.

Example 2

Preparation of poly(meth)acrylate Coated Calcium Formate ($1^{st}$ TC-C and $1^{st}$ TC-D)

The general procedures outlined in Example 1 were used to apply EUDRAGIT®RS 30D polymer coating on calcium formate particles (commercially available from Fisher Scientific). The coated particles consisted 5% or 10% by weight polymer coating.

The release of calcium formate was measured according to the general procedures described in the test method, "Release of coated calcium formate". The results are tabulated in Table 2.

TABLE 2

| Time (min) | $1^{st}$ TC-C (5% coating) | $1^{st}$ TC-D (10% coating) |
|---|---|---|
| 0 | 0.0 | 0.0 |
| 2 | 49.4 | 18.8 |
| 5 | 67.8 | 45.3 |
| 10 | 93.2 | 73.3 |
| 20 | 98.6 | 91.4 |
| 30 | 99.6 | 94.9 |
| 45 | 99.6 | 96.9 |
| 60 | 99.6 | 98.7 |

FIG. 2 is a graphical plot of release profiles of poly(meth)acrylate coated calcium formate. These triggering compositions showed singular release profiles. And the release rate was controlled by the amount of coating polymer.

Example 3

Calcium Formate Coated with Cellulose Acetate ($1^{st}$ TC-E)

400g of calcium formate particles (commercially available from Fisher Scientific, particles size as shown in Table 4) were stirred in a Kitchen-aid mixer. 45 ml of cellulose acetate solution (EASTMAN™ CA-398-3, 20% in acetone) was added onto the particles dropwise using a syringe over a period of two minutes. After stirring the mixture for one minute, the coated particles were air-dried then dried in oven at 50° C. for two hours.

The dried material was sieved to remove particles greater than 850 μm and smaller than 150 μm. The release profile of calcium formate was measured according to the general procedure described in the test method, "Release of coated calcium formate". The results are tabulated in Table 3.

Example 4

Calcium Formate Coated with Cellulose Acetate and Ethyl Cellulose ($1^{st}$ TC-F)

400g of calcium formate particles (commercially available from Fisher Scientific, particles size as shown in Table 4) were stirred in a Kitchen-aid mixer. 60 ml of cellulose acetate solution ((EASTMANTM CA-398-3, 20% in acetone) was added onto the particles dropwise using a syringe over a period of two minutes. After stirring the mixture for one minute, the coated particles were air-dried. Then the particles were coated with 70 ml of ethyl cellulose solution (commercially available from Sigma-Aldrich, 10 cP, 20% in ethanol) in the same manner to give a second layer of coating. Then the sample was dried in oven at 50° C. for two hours. The dried material was sieved to remove particles greater than 850 μm and smaller than 150 μm. The release profile of calcium formate was measured according to the general procedure described in the test method, "Release of coated calcium formate". The results are tabulated in Table 3.

TABLE 3

| Time (min) | $1^{st}$ TC-E | $1^{st}$ TC-F |
|---|---|---|
| 0 | 0.0 | 0.0 |
| 2 | 60.8 | 7.3 |
| 5 | 92.1 | 12.6 |
| 10 | 98.1 | 22.5 |
| 15 | 99.2 | 30.5 |

TABLE 3-continued

| Time (min) | 1$^{st}$ TC-E | 1$^{st}$ TC-F |
|---|---|---|
| 20 | 99.3 | 37.1 |
| 30 | 99.3 | 51.3 |
| 45 | 99.9 | 60.7 |
| 60 | 99.4 | 64.0 |
| 120 | 99.2 | 71.1 |

FIG. 3 is a graphical plot of release profiles of cellulose acetate or cellulose acetate/ethyl cellulose coated calcium formate. These triggering compositions showed singular release profiles.

Example 5

Preparation of Sodium Carboxymethyl Cellulose Coated Calcium Formate (1$^{st}$ TC-G)

400 g of calcium formate particles (commercially available from Fisher Scientific, particles size as shown in Table 4) were stirred in a Kitchen-aid mixer. 40 ml of sodium carboxymethyl cellulose (CMC) solution (1% in water) was added onto the particles dropwise using a syringe over a period of one minute. After stirring the mixture for one additional minute, the coated particles were dried in oven at 110° C. for 30 minutes. Then the sample was sieved using 20/80 mesh sieves (U.S. Sieve Series). The particles on the 80 mesh sieve were collected to afford 320 grams of product. The coated particles showed fast release rate in water, 77% released at one minute, 100% released at 2 minutes. The coated sample had larger particle size than the uncoated sample, as shown in Table 4.

TABLE 4

Particle size distribution of CMC coated calcium formate (1$^{st}$ TC-G)

| Sample | 850-300 microns (%) | 300-180 microns (%) | <180 microns (%) |
|---|---|---|---|
| Commercial calcium formate | 8 | 32 | 60 |
| 1$^{st}$ TC-G (CMC coated calcium formate) | 77.4 | 22.5 | 0.1 |

Example 6

Preparation of poly(meth)acrylate Coated Sodium Carbonate (2$^{nd}$ TC-A to 2$^{nd}$ TC-D)

The general procedures outlined in Example 1 were used to apply EUDRAGIT®RS 30D polymer coating on sodium carbonate particles (commercially available from Sigmal-Aldrich, particle size between 100-20 mesh, U.S. Sieve Series). The coated particles consisted 5%, 10%, 18%, or 27% by weight polymer coating.

The release of sodium carbonate was measured according to the general procedures described in the test method, "Release of coated sodium carbonate". The results are tabulated in Table 5

TABLE 5

| Time (min) | 2$^{nd}$ TC-A (5% coating) | 2$^{nd}$ TC-B (10% coating) | 2$^{nd}$ TC-C (18% coating) | 2$^{nd}$ TC-D (27% coating) |
|---|---|---|---|---|
| 0 | 0.0 | 0.0 | 0.0 | 0.0 |
| 2 | 3.6 | 0.3 | 0.4 | 0.2 |
| 4 | 9.5 | 0.6 | 0.5 | 0.3 |
| 6 | 15.7 | 1.1 | 0.7 | 0.4 |
| 8 | 22.1 | 1.8 | 0.8 | 0.4 |
| 10 | 28.4 | 3.6 | 1.0 | 0.5 |
| 15 | 43.5 | 10.4 | 1.5 | 0.8 |
| 20 | 56.5 | 17.3 | 3.9 | 1.0 |
| 25 | 66.8 | 25.0 | 8.1 | 1.4 |
| 30 | 75.2 | 32.3 | 12.9 | 2.1 |
| 40 | 86.1 | 47.5 | 22.6 | 5.9 |
| 50 | 91.9 | 60.6 | 32.6 | 12.7 |
| 60 | 95.0 | 71.6 | 42.5 | 20.2 |
| 80 | 99.0 | 86.0 | 61.3 | 35.6 |
| 100 |  | 92.4 | 76.3 | 49.4 |
| 120 |  | 96.1 | 84.7 | 60.0 |
| 150 |  |  | 89.9 | 72.9 |
| 210 |  |  | 98.9 | 94.8 |
| 280 |  |  |  | 99.8 |

FIG. 4 is a graphical plot of release profiles of poly(meth)acrylate coated sodium carbonate. These triggering compositions showed sigmoidal release profiles.

Example 7

Preparation of MPP Coated Sodium Carbonate (2$^{nd}$ TC-E, 2$^{nd}$ TC-F)

400 g of sodium carbonate particles (100-20 mesh) was put in a one-gallon plastic bucket. The bucket was placed on a Retch Shaker to fluidize the particles. Maleated polypropylene (MPP) emulsion (20% in water, commercially available from CHEMCOR, Chester, N.Y.) was sprayed onto particles using a spraying gun over a period of 20 minutes. The coated particles were dried in oven at 50° C. for 2 days. The coated particles consisted of 2% or 6% by weight of polymer coating.

The release of sodium carbonate was measured according to the general procedures described in the test method, "Release of coated sodium carbonate". The results are tabulated in Table 6.

TABLE 6

| Time | 2$^{nd}$ TC-E (2% coating) | 2$^{nd}$ TC-F (6% coating) |
|---|---|---|
| 0 | 0.0 | 0.0 |
| 2 | 20.2 | 17.7 |
| 5 | 42.1 | 26.9 |
| 10 | 69.5 | 48.6 |
| 15 | 87.8 | 61.4 |
| 20 | 95.7 | 81.1 |
| 30 | 99.1 | 94.1 |
| 40 | 99.6 | 96.2 |
| 60 | 100.0 | 96.2 |

FIG. 5 is a graphical plot of release profiles of maleated polypropylene coated sodium carbonate. These triggering compositions showed singular release profiles.

Examples 8-13

SAP Swelling/Deswelling by Forming Insoluble Salts

FAVOR ®SXM-9300, a commercially available superabsorbent polymer composition manufactured by Evonik Stockhausen Inc., Greensboro, N.C., was used to demonstrate the swelling and deswelling triggered by formation of insoluble salts. The superabsorbent polymer was first exposed to a salt solution containing multivalent cations.

Then it was exposed to a second salt solution containing anions which is able to complex with the multivalent cations of the first salt to form an insoluble salt having solubility product constant $Ksp<10^{-5}$. In comparative example 13, KCl was used as the first triggering chemical and $Na_2SO_4$ as the second triggering chemical.

Specifically, 0.20 g of superabsorbent polymer composition was placed in a teabag. The first centrifuge retention capacity of the superabsorbent polymer sample was tested according to the standard test method. Then the teabag was immersed in a deswell solution which was prepared by dissolving specific amount of the first triggering chemical in 10 g of 0.9% by weight sodium chloride solution. After 10 minutes of soaking time, the bag was placed in a centrifuge and the retention capacity was measured to give the second centrifuge retention capacity. Then the bag was immersed in a reswell solution which was prepared by dissolving specific amount of the second triggering chemical in 20 g of 0.9% by weight sodium chloride solution. After 20 minutes of soaking time, the bag was placed in a centrifuge and the retention capacity was measured to give the third centrifuge retention capacity. Results of the testing are summarized in Table 7. Solubility Product Constants listed in Table 7 refer to the salts formed from the cations of the first trigger chemical and the anions of the second trigger chemical. They are obtained from Professor Oliver Seely's, of California State University Dominguez Hills, Solubility Products database.

could reswell in presence of a second salt solution containing anions which are able to complex with the cations of the first salt to form an insoluble salt having solubility product constant $Ksp<10^{-5}$. In Example 13, the cations ($K^+$) of the first salt have an ionized valence of less than two and the anions ($SO_4^{2-}$) of the second salt form a soluble salt with the cations ($K^+$) of the first salt (KCl). In this case, the superabsorbent polymer failed to exhibit an effective deswell and reswell. Slightly reduced $2^{nd}$ and $3^{rd}$ CRC capacities are mainly due to salt poisoning effect caused by the soluble first and second salts.

Examples 14-16

SAP Swelling/Deswelling by Forming Insoluble Salts

Table 8 lists the swell/deswell/reswell evaluation results for SAP-B, SAP-D, and SAP-F from the centrifuge retention

TABLE 7

| Ex | SAP | 1st trigger chemical | $2^{nd}$ triggering chemical | Mixing ratio of SAP/$1^{st}$ chemical/$2^{nd}$ chemical | $1^{st}/2^{nd}/3^{rd}$ CRC (g/g) | Solubility Product Constant* |
|---|---|---|---|---|---|---|
| 8 | SXM9300 | $AlCl_3$ | $Na_5P_3O_{10}$ | 1/0.2/0.33 | 29.5/19.3/26.8 | $6.3 \times 10^{-19}$ |
| 9 | SXM9300 | $CaCl_2$ | $Na_2CO_3$ | 1/0.4/0.38 | 29.5/11.0/18.0 | $3.8 \times 10^{-9}$ |
| 10 | SXM9300 | $CaCl_2$ | $Na_5P_3O_{10}$ | 1/0.2/0.53 | 29.5/20.5/25.8 | $1 \times 10^{-26}$ |
| 11 | SXM9300 | $CaCl_2$ | $Na_5P_3O_{10}$ | 1/0.4/1 | 29.5/11.0/23.7 | $1 \times 10^{-26}$ |
| 12 | SXM9300 | calcium formate | $Na_2CO_3$ | 1/0.4/0.4 | 29.5/12.5/16.7 | $3.8 \times 10^{-9}$ |
| 13 | SXM9300 | KCl | $Na_2SO_4$ | 1/0.4/0.4 | 29.5/26/26 | $>10^{-5}$ |

The results from Examples 8-12 demonstrated the ability to deswell SAP by exposing the swollen SAP to a salt solution comprising cations having an ionized valence of two or more. In addition, the results also showed that the deswelled SAP capacity test. Superabsorbent polymers with lower degree of neutralization (SAP-D and SAP-F, 40-60% DN) demonstrated improved reswelling capacity compared with the SAP having regular degree of neutralization (about 70% DN).

TABLE 8

| Ex | SAP | 1st triggering chemical | $2^{nd}$ triggering chemical | Mixing ratio of SAP/$1^{st}$ chemical/$2^{nd}$ chemical | $1^{st}/2^{nd}/3^{rd}$ CRC (g/g) | Solubility Product Constant* |
|---|---|---|---|---|---|---|
| 14 | SAP-B | calcium formate | $Na_2CO_3$ | 1/0.3/0.6 | 29.4/16.0/20.7 | $3.8 \times 10^{-9}$ |
| 15 | SAP-D | calcium formate | $Na_2CO_3$ | 1/0.3/0.6 | 29.4/16.1/22.6 | $3.8 \times 10^{-9}$ |
| 16 | SAP-F | calcium formate | $Na_2CO_3$ | 1/0.2/0.2 | 33/26.5/31.8 | $3.8 \times 10^{-9}$ |

Examples 17-21

Swelling/Deswelling of Low DN Superabsorbent Polymers

Superabsorbent polymers having 40-60% of the degree of neutralization (DN) were used to demonstrate the mass efficiency and reswelling capacity improvement over the commercial available superabsorbent polymers, such as SXM-9300. Sulfamic acid was used as the first triggering chemical and sodium carbonate was used as the second triggering chemical. The evaluations were performed following the general procedures as described in Examples 8-13. The results are tabulated in Table 9.

TABLE 9

| Ex | SAP | $1^{st}$ triggering chemical | $2^{nd}$ triggering chemical | Mixing ratio of SAP/$1^{st}$ chemical/$2^{nd}$ chemical | $1^{st}/2^{nd}/3^{rd}$ CRC (g/g) |
|---|---|---|---|---|---|
| 17 | SAP-A SXM9300 | Sulfamic acid | Na$_2$CO$_3$ | 1/0.4/0.4 | 29.5/17.9/26.2 |
| 18 | SAP-C | Sulfamic acid | Na$_2$CO$_3$ | 1/0.2/0.4 | 30/21.9/31.2 |
| 19 | SAP-C | Sulfamic acid | Na$_2$CO$_3$ | 1/0.4/0.4 | 30/14.1/29.9 |
| 20 | SAP-E | Sulfamic acid | Na$_2$CO$_3$ | 1/0.2/0.4 | 29.1/18/29.5 |
| 21 | SAP-E | Sulfamic acid | Na$_2$CO$_3$ | 1/0.4/0.4 | 29.1/11/29.9 |

As clearly seen in Table 9, superabsorbent polymers with lower degree of neutralization (SAP-C and SAP-E) showed improved reswelling capacity and mass efficiency compared with the polymer with regular degree of neutralization, such as SXM-9300.

Example 22

Absorbent compositions comprising SXM-9300 and poly(meth)acrylate coated sulfamic acid were used to demonstrate the swelling/deswelling behavior of the absorbent composition. A mixture of SXM-9300 and coated sulfamic acid (triggering compositions $1^{st}$ TC-A or $1^{st}$ TC-B) was placed in a cylinder with screen bottom and the absorption capacity was measured according to the general procedures described in the "Swell/Deswell/Reswell test of the absorbent composition". The results are tabulated in Table 10.

TABLE 10

| SAP | Triggering composition | Wt. ratio of SAP and triggering composition | Starting point of deswelling step (min) | Maximum swelling capacity (g/g) |
|---|---|---|---|---|
| SXM-9300 | $1^{st}$ TC-A | 1/1.6 | 11 | 26 |
| SXM-9300 | $1^{st}$ TC-A | 1/1.2 | 13.5 | 27.4 |
| SXM-9300 | $1^{st}$ TC-A | 1/0.8 | 14.6 | 29 |
| SXM-9300 | $1^{st}$ TC-B | 1/1.2 | 33 | 33.5 |

From the results in Table 10 and FIG. 6, it can be seen that the swelling capacity and deswelling time was controlled by the polymer coating level in the triggering composition as well as by the mixing ratio of SAP and the triggering composition.

Examples 23-27

Table 11 lists the absorbent compositions comprising a superabsorbent polymer composition, a first triggering composition comprising sulfamic acid, and a second triggering composition comprising a basic material such as sodium carbonate. The swell/deswell/reswell curves were measured according to the general procedures described in the "Swell/Deswell/Reswell test of the absorbent composition".

TABLE 11

Absorbent compositions having triggering compositions

| Examples | Superabsorbent Polymer | First Triggering composition | First Triggering composition | Ratio |
|---|---|---|---|---|
| 23 | SXM-9300 | $1^{st}$ TC-A | $2^{nd}$ TC-B | 1:1.2:1.2 |
| 24 | SXM-9300 | $1^{st}$ TC-A | $2^{nd}$ TC-C | 1:1.2:1.2 |
| 25 | SAP-B | $1^{st}$ TC-A | $2^{nd}$ TC-B | 1:1.2:1.2 |
| 26 | SAP-C | $1^{st}$ TC-A | $2^{nd}$ TC-B | 1:0.6:1 |
| 27 | SAP-D | $1^{st}$ TC-A | $2^{nd}$ TC-B | 1:0.6:1 |

FIG. 7 is a graphical plot of swell/deswell/reswell curves of a dry mixture of SXM-9300 with both the first and second triggering compositions for Examples 23-24 and as shown in Table 11. In these examples, the starting point for the reswelling step was controlled by the release rate of the second triggering composition.

FIG. 8 is a graphical plot of swell/deswell/reswell curves for Example 25 and as shown in Table 11. In this example, SAP-B, a superabsorbent polymer composition comprising an encapsulated blowing agent, gave improved swelling capacity due to fast absorption rate compared with SXM-9300.

FIG. 9 is a graphical plot of swell/deswell/reswell curves for Examples 26-27 and as shown in Table 11. In these examples, SAP-C and SAP-D, superabsorbent polymer compositions having about 50% DN, afforded improved swelling and reswelling capacities and mass efficiency compared with SXM-9300. SAP-D exhibits an improved swelling capacity than SAP-C also due to its fast absorption rate.

Examples 28-32

Table 12 summarizes the absorbent compositions comprising a superabsorbent polymer composition, a first triggering composition comprising multivalent cations, and a second triggering composition comprising anions which are able to complex with the multivalent cations of the first triggering composition to form an insoluble salt having solubility product constant $K_{sp}<10^{-5}$. The swell/deswell/reswell curves were measured according to the general procedures described in the "Swell/Deswell/Reswell test of the absorbent composition".

TABLE 12

Absorbent compositions having triggering compositions

| Examples | Superabsorbent Polymer | First Triggering composition | First Triggering composition | Ratio |
|---|---|---|---|---|
| 28 | SXM-9300 | $1^{st}$ TC-C | $2^{nd}$ TC-A | 1:0.8:1.6 |
| 29 | SAP-B | $1^{st}$ TC-C | $2^{nd}$ TC-A | 1:1:1.2 |
| 30 | SAP-B | $1^{st}$ TC-F | $2^{nd}$ TC-C | 1:1:1 |
| 31 | SAP-D | $1^{st}$ TC-F | $2^{nd}$ TC-C | 1:0.4:0.8 |
| 32 | SAP-D | $1^{st}$ TC-F | $2^{nd}$ TC-C | 1:0.5:1 |

FIG. 10 is a graphical plot of swell/deswell/reswell curves for Example 28 and as shown in Table 12 as measured by Swell/deswell/Reswell Test. In this example, the superabsorbent polymer exhibited swell/deswell/reswell behavior after exposure to 0.9% saline solution.

FIG. 11 is a graphical plot of swell/deswell/reswell curves for Examples 29-30 and as shown in Table 12 as measured by Swell/Deswell/Reswell Test. In these examples, SAP-B, a superabsorbent polymer composition comprising an encapsulated blowing agent, afforded improved swelling capacity compared with SXM-9300.

FIG. 12 is a graphical plot of swell/deswell/reswell curves for Examples 31-32 and as shown in Table 12 as measured by Swell/Deswell/Reswell Test. In these examples, SAP-D, a superabsorbent polymer composition comprising an encapsulated blowing agent and having about 50% DN, demonstrated the advantage of improved swelling and reswelling capacity and mass efficiency improvement.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

What is claimed:

1. An absorbent composition comprising:
   a. a superabsorbent polymer composition comprising poly (acrylic acid) wherein said superabsorbent polymer composition has a degree of neutralization of less than about 70 molar per cent and a pH of less than about 6 wherein the superabsorbent polymer composition is a water-swellable, water-insoluble material and having a centrifuge retention capacity of at least about 25g/g;
   b. a first triggering composition for deswelling a swollen superabsorbent polymer composition which has absorbed liquid to form a deswelled superabsorbent polymer composition wherein the first triggering composition comprises a first water-soluble chemical comprising cations X having an ionized valence of two or more; and
   c. a second triggering composition for reswelling the deswelled superabsorbent polymer composition wherein the second triggering composition comprises a second water-soluble chemical comprising anions Y;
wherein the first water-soluble chemical and the second water-soluble chemical are encapsulated with a coating selected from a polymeric coating material which is selected from poly(meth)acrylate copolymers, polyacrylate copolymers, ethyl cellulose, sodium carboxymethylcellulose, cellulose acetate, polyethylene glycol, maleated polypropylene, polyolefin copolymers, or combinations thereof; and wherein the cations X of the first water-soluble chemical are capable of complexing with the anionic functional groups of the superabsorbent polymer composition; and the anions Y of the second water-soluble chemical are capable of complexing with the cations X to form a salt having a solubility product constant Ksp<$10^{-5}$.

2. The absorbent composition of claim 1 comprising from about 10 to about 90 wt % of said superabsorbent polymer composition, from about 5 to about 60 wt % of said first triggering composition, and from about 5 to about 60 wt % of said second triggering composition.

3. The absorbent composition of claim 1 wherein the superabsorbent polymer composition and the first and second triggering compositions are in particle form and the particle size is in the range from about 150μm to about 850μm.

4. The absorbent composition of claim 1 wherein the first triggering composition comprises a water-soluble chemical selected from aluminum chloride, aluminum sulfate, barium chloride, calcium acetate, calcium chloride, calcium formate, magnesium acetate, magnesium chloride, magnesium formate, zinc acetate, zinc chloride, zinc formate, and zinc sulfate.

5. The absorbent composition of claim 1 wherein the second triggering composition comprises a water-soluble chemical selected from sodium fluoride, sodium hydrogen carbonate, sodium carbonate, sodium citrate, sodium oxalate, sodium phosphate, sodium polyphosphate, sodium sulfide, sodium sulfate, or sodium tripolyphosphate.

6. The absorbent composition of claim 1 wherein said superabsorbent polymer composition comprising partially neutralized crosslinked poly(acrylic acid) having from about 40 to about 60 molar percent of the neutralized acidic functional groups.

7. The absorbent composition of claim 1 wherein the superabsorbent polymer composition has a vortex time of 45 seconds or less.

8. The absorbent composition of claim 1 wherein the first and second triggering compositions have a selected release profile respectively for releasing the water-soluble chemical after exposure to aqueous fluid and the first water-soluble chemical has higher cumulative release than the second water-soluble chemical before the first water-soluble chemical is 100% released.

9. The absorbent composition of claim 8 wherein the release profile is selected from singular release profile or sigmoidal release profile.

10. The absorbent composition of claim 8 wherein from about 50 wt % to 100 wt % of the water-soluble solid chemical is released from the first and second triggering compositions in less than about 240 minutes after exposure to aqueous liquid.

11. The absorbent composition of claim 1 wherein the superabsorbent polymer composition comprises from about 0.05 to about 10.0 wt % of a blowing agent.

12. The absorbent composition of claim 11 wherein the blowing agent comprising a carbonate or compound thereof.

13. The absorbent composition of claim 11 wherein the blowing agent is encapsulated with a resin which is selected from natural or synthetic resins, acrylonitrile-butadiene rubbers, viscous settable ceramic materials, polyolefins, polyethylene gylcol, olefin copolymers, polyaromatic olefins, styrenic compounds or polymerized halo-diolefins.

14. The absorbent composition of claim 13 wherein the resin comprises polyethylene glycol.

15. An absorbent composition comprising:
   a. a superabsorbent polymer composition comprising poly (acrylic acid) wherein said superabsorbent polymer composition has a degree of neutralization of less than about 70 molar per cent and a pH of less than about 6 wherein the superabsorbent polymer composition is a water-swellable, water-insoluble material and having centrifuge retention capacity of at least about 25g/g;
b. a first triggering composition for deswelling a swollen superabsorbent polymer composition which has absorbed liquid to form a deswelled superabsorbent polymer composition wherein the first triggering composition comprises a first water-soluble chemical comprising cations X having an ionized valence of two or more selected from calcium formate; and
c. a second triggering composition for reswelling the deswelled superabsorbent polymer composition wherein the second triggering composition comprises a second water-soluble chemical comprising anions Y selected from sodium carbonate;
wherein the first water-soluble chemical and the second water-soluble chemical are encapsulated with a coating selected from a polymeric coating material which is selected from poly(meth)acrylate copolymers, polyacrylate copolymers, ethyl cellulose, sodium carboxymethylcellulose, cellulose acetate, polyethylene glycol, maleated polypropylene, polyolefin copolymers, or combinations thereof; and
wherein the cations X of the first water-soluble chemical are capable of complexing with the anionic functional groups of the superabsorbent polymer composition; and the anions Y of the second water-soluble chemical are capable of complexing with the cations X to form a salt having a solubility product constant Ksp<10-5.

16. An absorbent composition comprising:
a. a superabsorbent polymer composition comprising poly(acrylic acid) wherein the superabsorbent polymer composition has a degree of neutralization of less than about 70 molar percent and a pH of less than about 6, the superabsorbent polymer composition comprising a blowing agent wherein the superabsorbent polymer composition is a water-swellable, water-insoluble material and having a centrifuge retention capacity of at least about 25g/g;
b. a first triggering composition for deswelling a swollen superabsorbent polymer composition which has absorbed liquid to form a deswelled superabsorbent polymer composition wherein the first triggering composition comprises a first water-soluble solid chemical comprising cations X having an ionized valence of two or more, wherein the first triggering composition has a release profile for releasing the water-soluble solid chemical from the triggering composition wherein the release profile is selected from a singular release profile or a sigmoidal release profile; and
c. a second triggering composition for reswelling the deswelled superabsorbent polymer composition wherein the second triggering composition comprises a second water-soluble solid chemical wherein the second triggering composition has a sigmoidal release profile for releasing the second water-soluble solid chemical from the triggering composition;
wherein the first water-soluble chemical and the second water-soluble chemical are encapsulated with a coating selected from a polymeric coating material which is selected from poly(meth)acrylate copolymers, polyacrylate copolymers, ethyl cellulose, sodium carboxymethylcellulose, cellulose acetate, polyethylene glycol, maleated polypropylene, polyolefin copolymers, or combinations thereof; and wherein the first water-soluble chemical has higher cumulative release than the second water-soluble chemical after exposure to aqueous fluid and before about 100% release.

17. The absorbent composition of claim 16 wherein said superabsorbent polymer composition comprising partially neutralized crosslinked poly(acrylic acid) having from about 40 to about 60 molar percent of the neutralized acidic functional groups.

18. The absorbent composition of claim 16 wherein said first water-soluble chemical is calcium formate and said second water-soluble chemical is sodium carbonate.

19. An absorbent composition comprising:
a. a superabsorbent polymer composition comprising crosslinked poly(acrylic acid) and having a first absorption capacity; wherein the superabsorbent polymer composition has a degree of neutralization of less than about 70 molar percent and has a pH of less than about 6 wherein the superabsorbent polymer composition is a water-swellable, water-insoluble material and having a centrifuge retention capacity of at least about 25g/g;
b. a first triggering composition for deswelling the swollen superabsorbent polymer composition which has absorbed liquid to form a deswelled superabsorbent polymer composition wherein the first triggering composition comprises a first water-soluble chemical comprising cations X having an ionized valence of two or more; and
c. a second triggering composition for reswelling the deswelled superabsorbent polymer composition wherein the second triggering composition comprises a second water-soluble chemical comprising anions Y;
wherein the first water-soluble chemical and the second water-soluble chemical are encapsulated with a coating selected from a polymeric coating material which is selected from poly(meth)acrylate copolymers, polyacrylate copolymers, ethyl cellulose, sodium carboxymethylcellulose, cellulose acetate, polyethylene glycol, maleated polypropylene, polyolefin copolymers, or combinations thereof; and
wherein the superabsorbent polymer composition and the first and second triggering compositions are in particle form, and the superabsorbent polymer composition particles and the first and second triggering composition particles have a particle size of from more than about 150 μm to less than about 1000 μm.

20. The absorbent composition of claim 19 wherein the superabsorbent polymer composition and the first and second triggering compositions have a particle size from about 150 μm to about 850 μm and wherein when the absorbent composition is contacted with a fluid that causes the superabsorbent polymer composition to absorb the fluid to form a swollen superabsorbent polymer composition, and the first triggering composition is combined with the swollen superabsorbent polymer results in the swollen superabsorbent polymer composition deswelling a portion of the fluid from the swollen superabsorbent polymer composition, and the resulting deswelled swollen superabsorbent polymer composition has a second absorption capacity that is about 20% or more less than the first absorption capacity; and wherein when the second triggering composition contacts the combination of the swollen superabsorbent polymer composition and first triggering composition of b) the resulting superabsorbent polymer composition has a third absorption capacity that is greater than the second absorption capacity.

21. The absorbent composition of claim 19 wherein said first water-soluble chemical is calcium formate and said second water-soluble chemical is sodium carbonate.

22. An absorbent composition comprising:
   a. a superabsorbent polymer composition comprising poly(acrylic acid) wherein the superabsorbent composition has a degree of neutralization of less than about 70 molar percent and a pH of less than about 6 wherein the superabsorbent polymer composition is a water-swellable, water-insoluble material and having a centrifuge retention capacity of at least about 25 g/g; and
   b. a triggering composition comprising a water-soluble solid chemical wherein said triggering composition comprises a water-soluble chemical comprising cations X having an ionized valence of two or more and wherein the triggering composition has a release profile for releasing the water-soluble solid chemical from the triggering composition wherein the release profile is selected from a singular release profile or a sigmoidal release profile,
   wherein the water-soluble chemical is encapsulated with a coating selected from a polymeric coating material which is selected from poly(meth)acrylate copolymers, polyacrylate copolymers, ethyl cellulose, sodium carboxymethylcellulose, cellulose acetate, polyethylene glycol, maleated polypropylene, polyolefin copolymers, or combinations thereof; and wherein the superabsorbent polymer composition and the triggering composition are in particle form, and the superabsorbent polymer composition particles and the triggering composition particles have a particle size of from more than about 150 μm to less than about 1000 μm.

23. The absorbent composition of claim 22 wherein said first water-soluble chemical is calcium formate and said second water-soluble chemical is sodium carbonate.

\* \* \* \* \*

UNITED STATES PATENT AND TRADEMARK OFFICE
CERTIFICATE OF CORRECTION

PATENT NO. : 8,318,306 B2  
APPLICATION NO. : 12/022699  
DATED : November 27, 2012  
INVENTOR(S) : Gonglu Tian et al.

It is certified that error appears in the above-identified patent and that said Letters Patent is hereby corrected as shown below:

Column 30,  
Line 46, "((EASTMANTM CA-398-3," should read -- ((EASTMAN™ CA-398-3, --.

Column 39,  
Lines 1-2, "water-insoluble material and having centrifuge" should read -- water-insoluble material and having a centrifuge --.

Line 29, "constant Ksp<10-5." should read -- constant $K_{sp}<10^{-5}$. --.

Signed and Sealed this  
Twenty-ninth Day of January, 2013

David J. Kappos  
*Director of the United States Patent and Trademark Office*